United States Patent [19]
Gale et al.

[11] Patent Number: 5,273,884
[45] Date of Patent: Dec. 28, 1993

[54] POLYPEPTIDES, ANTIGENS OR VACCINES PROTECTIVE AGAINST BABESIOSIS

[75] Inventors: Kevin G. Gale, Brisbane; David J. Waltisbuhl, Queensland; Ian G. Wright, Brisbane; Brian V. Goodger, New South Wales, all of Australia

[73] Assignee: Commonwealth Scientific & Industrial

[21] Appl. No.: 470,284

[22] Filed: Jan. 25, 1990

[30] Foreign Application Priority Data

Jan. 25, 1989 [AU] Australia ............................... PJ2427
Nov. 16, 1989 [AU] Australia ............................... PJ7722

[51] Int. Cl.$^5$ ..................... G01N 33/53; C07K 15/28; A61K 39/00; C07H 21/02
[52] U.S. Cl. ...................................... 435/7.1; 424/88; 435/7.22; 435/691; 530/388.1; 530/388.6; 530/350; 536/23.1
[58] Field of Search .................... 435/6, 7.1, 7.2, 69.1, 435/7.22; 435/69.1; 530/388.1; 530/388.6; 240.27, 252.3, 252.33, 7.22; 436/501, 519, 548, 63; 530/387, 809; 536/26, 27, 28, 29, 23.1; 935/65, 95, 102, 106; 424/88

[56] References Cited

U.S. PATENT DOCUMENTS 4,596,707  6/1986  Ristic et al. ........................... 424/88

OTHER PUBLICATIONS

Timms et al. Res. Vet. Sci. 45:267-269 (1988).
Gill et al., Molec. Biochem. Parasitol. 22: 195-202 (1987).

*Primary Examiner*—Stephanie W. Zitomer
*Attorney, Agent, or Firm*—Sughrue, Mion Zinn Macpeak & Seas

[57] ABSTRACT

An antigen which produces immunity against homologous or heterologous challenge with babesia of cattle. The antigen is immunoreactive with a monoclonal antibody or polyclonal antisera recognising a protein located on the surface of babesia-infected erythrocytes and within a spherical or mitochondrion like organelle. The antigen can be prepared by (i) preparing nucleic acids from babesia infected erythrocytes depleted of leucocytes; (ii) forming a cDNA or genomic library from nucleic acids obtained in step (i); (iii) screening said library formed in step (ii) with a suitable probe to identify clones of interest; and thus providing DNA inserts for an expression vector which may be used to transform an appropriate host; (iv) obtaining a recombinant polypeptide from said transformed hosts which is protective against babesiosis. A monoclonal antibody reactive with the antigen, a DNA sequence which produces a protein protective against babesiosis when administered as a vaccine, and a vaccine including the antigen in combination with an adjuvant is also included in the inventive concept.

43 Claims, 21 Drawing Sheets

```
First nt.
   +1    GAAGGAACTA TCCATGGTTC GGATTCGCAA ATCTCAAATG TGGAGTCAGA
         CTTCCTTGAT AGGTACCAAG CCTAAGCGTT TAGAGTTTAC ACCTCAGTCT +51    CAAACAGGTG ATAACGAAT  CTATTTTAAA TCCCGCAATT CGTTTCCCAA
         GTTTGTCCAC CTATTGCTTA GATAAAATTT AGGGCGTTAA GCAAAGGGTT +101    CGTTAATTGG CGACTCACAT GGTCATTCTC CTAGTGTTAA CGACTTGCAT
         GCAATTAACC GCTGAGTGTA CCAGTAAGAG GATCACAATT GCTGAACGTA +151    GGTTCTGATG TTGAGGCTGG AACGGATGGT ATGTTCGATG TAGGTGTAAC
         CCAAGACTAC AACTCCGACC TTGCCTACCA TACAAGCTAC ATCCACATTG +201    CGTTAACCAT TACTACGCGA ATGATGGTGA AGGAAATGCG CTATCTGTTC
         GCAATTGGTA ATGATGCGCT TACTACCACT TCCTTTACGC GATAGACAAG +251    CTGGCAAATC GGTTACCATT AACCATTATC ATCATCAGGT GACAGACGGG
         GACCGTTTAG CCAATGGTAA TTGGTAATAG TAGTAGTCCA CTGTCTGCCC +301    GAAACCAAAC CGGTGGTTGG AGAAAGTGTG GTTATTAGTT ACGAGAAGGA
         CTTTGGTTTG GCCACCAACC TCTTTCACAC CAATAATCAA TGCTCTTCCT +351    GCTTGACGAT ACCATGTCCA AGCAATTGAT GGGTGAAAGT GTGTCATTTG
         CGAACTGCTA TGGTACAGGT TCGTTAACTA CCCACTTTCA CACAGTAAAC +401    TTCACCACAA TAACGAAAAT GGCGACATTT ACGTTAACCC GGTCCTATCC
         AAGTGGTGTT ATTGCTTTTA CCGCTGTAAA TGCAATTGGG CCAGGATAGG +451    GATTTTATGA ATGTCTCTTA CAGTAACCCC AACGGCAAAG TCGATCTCTT
         CTAAAATACT TACAGAGAAT GTCATTGGGG TTGCCGTTTC AGCTAGAGAA +501    CGTTAATCCT CTCATTGCAG AAAACATTAA AATTAAGGAT GCCTTCTCAC
         GCAATTAGGA GAGTAACGTC TTTTGTAATT TTAATTCCTA CGGAAGAGTG +551    AAACAGAAGA CGTACTTCGT AATTGTGCTG TTATGCGTTT ACGCAAATT
         TTTGTCTTCT GCATGAAGCA TTAACACGAC AATACGCAAA TGCGGTTTAA +601    ATCAACTTAT TACCGGAAAA CATCTCAGAA CAGTTTATGT CACAAAATGT
         TAGTTGAATA ATGGCCTTTT GTAGAGTCTT GTCAAATACA GTGTTTTACA +651    ATTCAACTTC GACCATTACC TTGCTACTCA ACTGGGCAGT TTGCCTGGAG
         TAAGTTGAAG CTGGTAATGG AACGATGAGT TGACCCGTCA AACGGACCTC +701    GTAGTTTATC GGATGTGATA ATCAACCAAG TTACTAGACA CCTGGTGAAG
         CATCAAATAG CCTACACTAT TAGTTGGTTC AATGATCTGT GGACCACTTC
```

FIG. 17 CONT.'

```
First nt.
   +751   GAAATCCTTC ATAACCATGC GCAACACATT ACGGATGTTT CGGATGAGCG
          CTTTAGGAAG TATTGGTACG CGTTGTGTAA TGCCTACAAA GCCTACTCGC +801   CGAACTTGAA GCGTATCTAA CATACATAAT TAGCACAACA TTGGAACATT
          GCTTGAACTT CGCATAGATT GTATGTATTA ATCGTGTTGT AACCTTGTAA +851   CCACATTACC AGCAATGGCT CCCTACTGTA AGGGTCTTGA TATCTCTTCC
          GGTGTAATGG TCGTTACCGA GGGATGACAT TCCCAGAACT ATAGAGAAGG +901   AAGCTACGTT ATGAGCAGTT ATATAGGCTA TTGGCAGGGA AATCAGGTAA
          TTCGATGCAA TACTCGTCAA TATATCCGAT AACCGTCCCT TTAGTCCATT +951   CCAAAGGTTT AACCAGATTC TTTCACGTCT TGCTTCACAG TCCCCCGGGG
          GGTTTCCAAA TTGGTCTAAG AAAGTGCAGA ACGAAGTGTC AGGGGGCCCC +1001   CCGACACCAA TGAGGACTTT GAGGAGATGG TGACAAAGTT GAAGGATATA
          GGCTGTGGTT ACTCCTGAAA CTCCTCTACC ACTGTTTCAA CTTCCTATAT +1051   CCTAACATTG AGCTGCCCGC AGATATTCAA AAGCCATTAA GGATGATGCC
          GGATTGTAAC TCGACGGGCG TCTATAAGTT TTCGGTAATT CCTACTACGG +1101   ACCTGGCAAA TTGCCGACTG ATTTGGCCAG AGGACATTGC CCGTTATTTG
          TGGACCGTTT AACGGCTGAC TAAACCGGTC TCCTGTAACG GGCAATAAAC +1151   TCAGAAATGC TTTGAATAAC GAAACCGAGC AGCAATTATC TAAATTGAGA
          AGTCTTTACG AAACTTATTG CTTTGGCTCG TCGTTAATAG ATTTAACTCT +1201   GGGAATTACC ATTCAAATGT TCAAGATGCC GTTTCAAAGT ATATTTTGAA
          CCCTTAATGG TAAGTTTACA AGTTCTACGG CAAAGTTTCA TATAAAACTT +1251   CAGACTGCAG ACACCACATA TGGTTACCGT GGTTTGATCT AAGAATGCAT
          GTCTGACGTC TGTGGTGTAT ACCAATGGCA CCAAACTAGA TTCTTACGTA +1301   TTTTTATTTG ATTTTGGTTT ACATTCTACT GGAAGTATAA GCATTTATAA
          AAAAATAAAC TAAAACCAAA TGTAAGATGA CCTTCATATT CGTAAATATT +1351   TTGGTTCAAT ATTTTTAACG AACAACTATA TATACTAATG TATTATCAAT
          AACCAAGTTA TAAAAATTGC TTGTTGATAT ATATGATTAC ATAATAGTTA

+1401   TAAAAAAAAA AAAA
          ATTTTTTTTT TTTT
```

FIG. 18

```
  1 glu-gly-thr-ile-his-gly-ser-asp-ser-gln-ile-ser-asn-val-glu-ser-asp-lys-gln-val-
 21 asp-asn-glu-ser-ile-leu-asn-pro-ala-ile-arg-phe-pro-thr-leu-ile-gly-asp-ser-his-
 41 gly-his-ser-pro-ser-val-asn-asp-leu-his-gly-ser-asp-val-glu-ala-gly-thr-asp-gly-
 61 met-phe-asp-val-gly-val-thr-val-asn-his-tyr-tyr-ala-asn-asp-gly-glu-gly-asn-ala-
 81 leu-ser-val-pro-gly-lys-ser-val-lys-ser-val-thr-ile-asn-his-tyr-his-gln-val-thr-asp-gly-
101 glu-thr-lys-pro-val-val-gly-glu-ser-val-val-ile-ser-val-gly-tyr-glu-lys-gln-leu-asp-asp-
121 thr-met-ser-lys-gln-leu-met-gly-glu-ser-val-phe-val-his-his-asn-asn-glu-asn-
141 gly-asp-ile-tyr-val-asn-pro-val-leu-ser-asp-phe-met-asn-val-ser-tyr-ser-asn-pro-
161 asn-gly-lys-val-asp-leu-phe-val-asn-pro-leu-ile-ala-glu-asn-ile-lys-ile-lys-asp-
181 ala-phe-ser-gln-thr-glu-asp-val-leu-arg-asn-cys-ala-val-met-arg-leu-arg-gln-ile-
201 ile-asn-leu-leu-pro-asn-ile-ser-glu-gln-phe-met-ser-gln-asn-val-phe-asn-phe-
221 asp-his-tyr-leu-ala-thr-gln-leu-gly-ser-leu-pro-gly-ser-leu-ser-asp-val-ile-
241 ile-asn-gln-val-thr-arg-his-leu-val-lys-glu-ile-leu-his-asn-his-ala-gln-his-ile-
261 thr-asp-val-ser-asp-glu-arg-gly-arg-ala-tyr-leu-thr-tyr-ile-ile-ser-thr-thr-
281 leu-glu-his-ser-thr-leu-pro-ala-met-ala-pro-tyr-cys-lys-gly-leu-asp-ile-ser-ser-
301 lys-leu-arg-tyr-glu-gln-leu-tyr-arg-leu-ala-gly-lys-ser-gly-asn-gln-arg-phe-
321 asn-gln-ile-leu-ser-arg-leu-ala-ser-gln-ser-pro-gly-ala-asp-thr-asn-glu-asp-phe-
341 glu-glu-met-val-thr-lys-leu-lys-asp-leu-pro-asn-ile-glu-leu-pro-ala-asp-ile-gln-
361 lys-pro-leu-arg-met-met-pro-pro-gly-lys-leu-pro-thr-asp-leu-ala-arg-gly-his-cys-
381 pro-leu-phe-val-arg-asn-ala-leu-asn-asn-glu-thr-gln-gln-leu-ser-lys-leu-arg-
401 gly-asn-tyr-his-ser-asn-val-asp-ala-val-ser-lys-tyr-ile-leu-asn-arg-leu-gln-
421 thr-pro-his-met-val-thr-val-val-STOP
```

FIG. 19

```
First nt.
    +1  GACCACGAGA CCGTTGAGCC TATAGTCTCT GACCACGAGA GTGTATCCAG
        CTGGTGCTCT GGCAACTCGG ATATCAGAGA CTGGTGCTCT CACATAGGTC +51  CGGTAGACCG TCTGAGGAAG AGGTTTCCGA GATTCCATCT
        GCCATCTGGC AGACTCCTTC TCCAAAGGCT CTAAGGTAGA
```

1 asp-his-glu-thr-val-glu-pro-ile-val-ser-asp-his-glu-ser-val-ser-ser-gly-arg-pro-
21 ser-glu-glu-glu-val-ser-glu-ile-pro-ser-

POLYPEPTIDES, ANTIGENS OR VACCINES PROTECTIVE AGAINST BABESIOSIS

FIELD OF INVENTION

This invention relates to DNA sequences, recombinant DNA molecules and processes for producing polypeptides or antigens eliciting antibodies proteotive against *Babesia parasitaemia* and babesiosis when administered to suitable animals suoh as *Bos taurus* cattle. This invention also relates to suoh polypeptides and antigens as well as vaccines produced from these polypeptides or related polypeptides or antigens whioh vaccines are highly protective against Babesia infection, or infection with any other parasite species.

More particularly, the invention relates to DNA sequences expressed in appropriate host organisms. The recombinant DNA molecules disclosed herein are characterised by DNA sequences that code for polypeptides whioh have the immunological activity of a polypeptide of *B. bovis* or any other species. A particular example of such a polypeptide is designated as antigen W11C5.

Antigen W11C5 is an antigen reactive with the monoclonal antibody secreted by hybridoma W11C5, which hybridoma was deposited with the European Collection of Animal Cell Cultures, Porton Down, Salisbury, Wiltshire, SP40JG, United Kingdom, on Dec. 16, 1988 under accession number 88121501 - W11C5.1.A5.F1-0.A2.

Accordingly, this invention further relates to hybridoma W11C5, the monoclonal antibody secreted by hybridoma W11C5 and antigens specifically reactive with this monoclonal antibody.

However it will be appreciated that the invention includes within its scope any monoclonal antibody derived from antigens related to antigen W11C5 eliciting antibodies protective against babesiosis and that therefore the invention is not restricted to the monoclonal antibody secreted by hybridoma W11C5. The invention also includes within its scope any hybridoma capable of producing the abovesaid monoclonal antibodies exemplified by hybridoma W11C5.

BACKGROUND OF THE INVENTION

*Babesia bovis* is the major causative agent of tick fever morbidity in domestic cattle ranged on tropical and subtropical pastures. Early work on the immunity conferred on infected animals which survived indicated that the immune response was humoral, since immunity was conferred to calves by colostrum immunoglobulins from infected mothers.

Unresolved antibodies from animals immune to *B. bovis* were subsequently shown to elicit immunity when transferred to non-immune animals.

Hitherto vaocines have been produced which protect cattle against the severe clinical manifestations of *B. bovis* parasitaemia. The vaccines used to date include those using killed *B. bovis*, live vaccines using *B. bovis* attenuated by either irradiation or rapid passage in splenectomized calves and vaccines derived from in vitro culture supernatant antigens. Although such vaccines are to some extent protective, they all have the inherent problem of containing many antigens. Vaccination with such vaccines therefore elicits an immune response which places the immune system of the vaccinated animal under considerable stress. Also, multi-antigenic vaocines may contain antigens which elicit a strong response activity but which are not especially proteotive due to the location or chemistry of the antigen in the virulent field strains. This strong response may mask or otherwise inhibit the development of immunity based on antibody response to the presence of a less reactive antigen capable in isolation of conferring protective immunity.

Where live attenuated vaccines are used, contamination of the vaccine with other pathogens may occur. Animals vaccinated with the live vaccines are subclinically infected carriers of the parasite and the potential for breakthrough infection due to de-attenuation is present. Refrigerated vaccine has a shelf life of only seven days.

In order to identify specific babesial antigens whioh confer protective immunity, babesial proteins from infected erythrocytes have been fractionated and assayed for immunoprotective potential. Protective antigens have been found in the soluble protein fraction obtained from lysis of babesia-infected erythrocytes as described in Australian patent specification No. 553779. Monoclonal antibodies have been raised against the protective soluble babesia protein fractions, and IFA, ELISA and Western blotting techniques used to identify clones producing monoclonal antibodies against specific babesial antigens. Antigens were then afiinity purified with the monoclonal antibodies to yield single antigens for vaccination testing.

Whilst purified antigen may be produced from babesial lysates by using the monoclonal antibody to that antigen, this method is not suitable for large scale production of vaccination grade product. The requirement therefore arises for improved commercial scale processes for the manufacture of antigen and polypeptides having like immunogenic activity. Attention has therefore been focused on the use of recombinant DNA techniques to transform nonbabesial hosts with babesial genes.

Kemp et al. (Mol. Biochem. Parasit., 12 (1984) 61-67) discloses that babesia genes can transform the eukaryotic yeast host *Saccharomyces cerevisiae*, and that the transformed host produces poly A+ RNAs corresponding to the transforming genes. However, there is no data to indicate that the polypeptides corresponding to the poly A+ mRNA obtained from K-strain *B. bovis*-infected erythrocytes were protective. The library was amplified in λ-gt10, cleaved, radiolabelled, fractionated, and re-ligated into an ampicillin-resistance-conferring expression vector λ-amp3. Phage were packaged in vitro and plated out on *E. coli* BTA282 on ampicillin-containing media, and colonies producing cDNA detected by colony hybridization. Colonies expressing babesia antigens were detected by autoradiography using bovine antiserum to $K_A$ strain *B. bovis* and $^{125}$I-labelled anti-bovine Ig. One clone was selected for further study (designated $K_A$Bb1). This clone produced a fusion protein of β-galactosidase and a babesial antigen 5-10 kDa larger than native β-galactosidase.

Anti-$K_A$ antisera were fractionated against the fusion protein to yield affinity-purified anti-$K_A$Bb1 antibodies. These antibodies were used to detect a 220 kDa antigen, corresponding to the dominant 220 kDa antigen detected by unfractionated serum. Immunofluorescent assay indicated that anti-$K_A$Bb1 reacts only with the Babesia parasite and not with the surrounding erythrocytic cytoplasm in vitro. By contrast, unfractionated anti-$K_A$ serum reacts with both the infected erythrocyte cytoplasm and the parasite.

However, vaccines formulated from the $K_ABb1/\beta$-galactosidase fusion protein did not exhibit significant protective immunization of animals against virulent heterologous *B. bovis* Challenge (Timms et al., unpublished results, Animal Research Institute, Queensland Department of Primary Industries). Indeed, the results indicated that the $K_ABb1/\beta$-galactosidase vaccines were less efficacious than live $K_A$ vaccines.

The whole approach adopted by Kemp in regard to location of polypeptides protective against babesiosis however was a "shotgun" approach and was not based on an approach which could be used to provide protective native as well as recombinant polypeptides.

Reference also may be made to Cowman described in Manipulation and Expression of Genes in Eukaryotes (1983) 185-188 wherein a gene coding for avirulence-associated polypeptides of *B. bovis* was isolated by differential colony hybridization.

Poly A+ RNA was isolated from K-avirulent (K-A) strain by extraction from parasitized cattle erythrocytes and oligo-dT cellulose chromatography. The RNA was copied into double-stranded cDNA which was inserted in pBR322. Transformed cells were plated on nitrocellulose filters and replica filters were hybridized with labelled cDNA probes synthesized from poly(A) RNA of K-A and the virulent K geographical isolate (K-V). cDNA plasmids were selected representing RNAs of differing abundance. Increased levels of RNA molecule were found to correlate with avirulence.

However, the main thrust of this reference was to identify cDNAs corresponding to RNAs which hybridize in greater abundance with probes synthesized from poly A+ mRNA of the avirulent Ka strain. This reference did not disclose however preparation of polypeptides.

SUMMARY OF THE INVENTION

The present invention in one aspect resolves at least some of the problems associated with the prior art by providing a process which serologically determines a protective antigen and also raising a monoclonal antibody to that antigen. The process also includes cloning DNA sequences that code for polypeptides at least partially homologous with that antigen and using said monoclonal antibody as a probe to isolate a cDNA clone expressing the desired polypeptide. The said process thereby provides DNA sequences, recombinant DNA molecules and methods for use of those sequences and molecules in the production of polypeptides displaying at least some of immunogenic activity of that antigen.

By virtue of this invention, it is possible to obtain polypeptides displaying an immunological activity of the W11C5 antigen, for use in protective immunisation of *Bos taurus* against clinical Babesiosis. This recombinant DNA produced polypeptide may also be used for the purpose of immunoassay and immunodiagnosis. This invention allows the production of a novel polypeptide or polypeptides derived, modified or otherwise produced from the novel polypeptide in amounts and by methods hitherto not available.

As will be appreciated from the disclosure to follow, the DNA sequences and recombinant DNA molecules of the invention are capable of directing the expression of a polypeptide displaying at least some of the immunological activity of the native W11C5 antigen. Replication of these DNA sequences and recombinant DNA molecules in appropriate hosts also provides a means of amplifying DNA to yield quantities of DNA coding for the polypeptide in hitherto unobtainable quantities. The molecular structure of these genes may thus be readily determined. The polypeptide and corresponding DNA is useful, either as produced in the host or after appropriate modification, in compositions and methods for detecting and improving the production of these products themselves and for use in immunoprotective, immunodiagnostic and immunoassay agents and methods.

The sequences of this invention are further characterised in that they permit the production of W11C5-like polypeptides in non-babesial hosts.

In another aspect of the present invention there is provided antigen purified by immunoreactivity with McAB11C5 (Ag11C5).

The invention also includes within its scope an anti-idiotypic antibody displaying at least some of the immunogenic activity of W11C5 antigen.

In yet another aspect of the present invention there is provided DNA sequences coding for polypeptides having at least some of the immunoreactivity of Ag11C5 wherein the sequences comprise cDNA sequences corresponding to babesial mRNAs having substantial homology with at least part of the *B. bovis* gene or genes coding for antigen W11C5.

Also within this aspect of the present invention are DNA sequences which hybridize to any of the foregoing DNA sequences, DNA sequences from whatever source including natural, synthetic or semisynthetic sources, related by mutations including single or multiple-base substitutions, deletions, insertions, inversions and 3' or 5' additions to any of the foregoing DNA sequences or inserts, and DNA sequences comprising sequences of codons which on expression code for a polypeptide displaying similar immunogenic properties to a polypeptide produced on expression of any of the foregoing DNA sequences.

In another aspect of the present invention are provided compositions comprising any of Ag11C5, McAb11C5 and polypeptides expressed as above together with an appropriate vehicle such as an adjuvant, whioh compositions are variously useful as vaccines, immunoassay reagents and immunodiagnosis reagents.

BRIEF DESCRIPTION OF THE DRAWINGS

FIG. 17 shows the unique region DNA sequence of W11C5 cDNA.

FIG. 18 shows the derived amino acid sequence of the W11C5 cDNA.

FIG. 19 shows the DNA sequence of a copy of the 90 base pair repeat and the derived amino acid sequence.

DETAILED DESCRIPTION OF THE INVENTION

Figure 1:
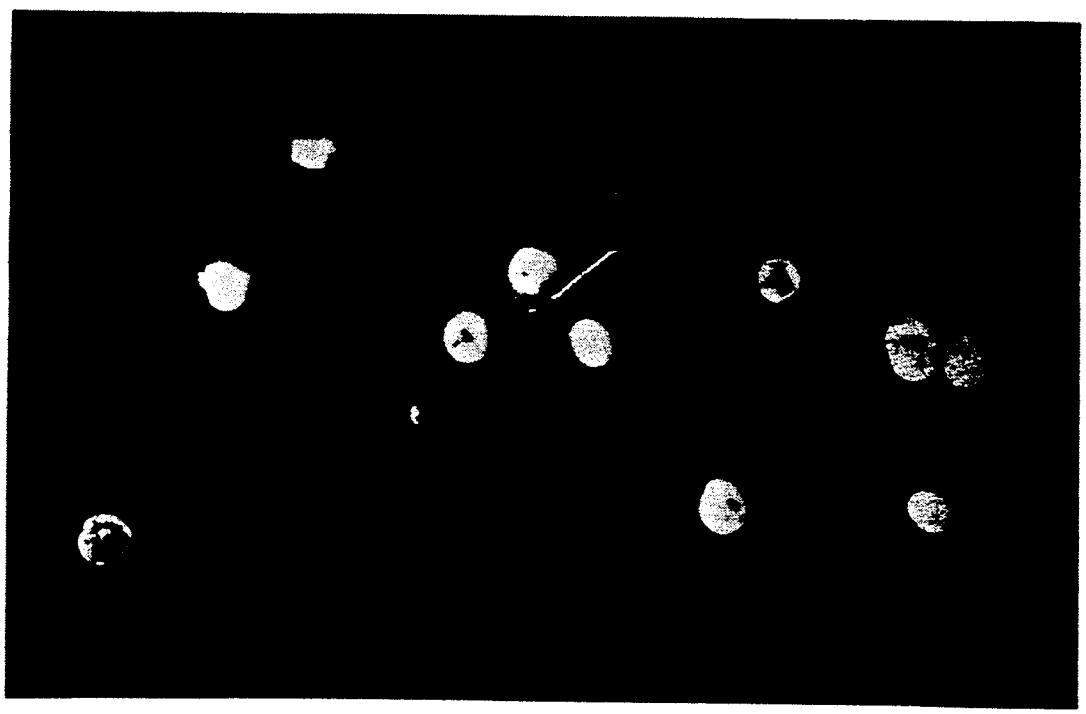
FIG. 1 is an Immunofluorescent Assay (IFA) depicting the staining pattern of MAb W11C5 against *Babesia bovis* infected erythrocytes.

The process used to generate the subject hybridoma W11C5, is described fully hereinafter. However it should be recognized that the hybridoma may have been derived by any other protocol known to the art. A broad description encompassing at least some of the available protocols involves the steps of:

(i) preparing nucleic acids from babesia infected erythrocytes depleted of leucocytes
(ii) forming a cDNA or genomic library from nucleic acids obtained in step (i)
(iii) screening said library formed in step (ii) with a suitable probe to identify clones of interest; and thus providing DNA inserts for an expression vector whioh may be used to transform an appropriate host
(iv) obtaining a recombinant polypeptide from said transformed hosts which is protective against babesiosis The stroma of Babesia-infected erythrocytes may be prepared in any suitable manner. For example, any of the following protocols may be employed
(i) osmotic lysis
(ii) mechanical disruption
(iii) cell disruption through proliferation of parasites or
(iv) cell lysis using lysins or antibodies.

Preferably the cell stroma are prepared by protocol (i) and in particular by any of the methods referred to in Mahoney (1967) Exp. Parasitol. 20, 232-41.

The parasites so prepared may be separated from the cytosol, resuspended and disrupted, preferably by sonication and the sonicate preferably ultracentrifuged to yield a supernatant containing soluble babesial antigens. This supernatant may be harvested to provide the crude mixture of soluble babesial antigens.

Monoclonal antibodies to the soluble babesia antigens prepared above may be prepared by any known method, including that described in Australian Patent number 553779. Preferably, the crude antigen mixture is administered to a suitable animal, for example, mice such that the animal elicits antibody-producing cells suoh as B-lymphocytes or splenocytes. The antibody-producing cells may be harvested. However, since the harvested cells age and die in culture, the cells are generally fused with immortal cells from the same species such as myeloma cells. This yields hybrid cells whioh excrete antibodies and are able to be cultured indefinitely.

It is particularly preferred to use BALB/c mice as the source of antibody producing cells, and to fuse the B-lymphocytes or splenocytes harvested therefrom with a mouse myeloma cell line such as P3-NSI-Ag4-1.

After fusion, the hybrid cells may be diluted out in a suitable medium suoh as RPMI1640 supplemented with IgG depleted foetal calf serum, and the diluted cells placed in for example a microtitre plate having a plurality of wells.

After a suitable growth time, the supernatant from each of the wells may be screened to identify wells producing antibody whioh is preferentially immunoreactive with infected erythrocytes. Screening may be performed by any known procedure including immunofluorescent assay (IFA) or enzyme-linked immunosorbent assay (ELISA).

The cells in the wells so identified may be recloned any number of times by limiting dilution with screening to yield a hybrid cell line producing a monoclonal antibody having the desired immunoreactivity with infected erythrocytes.

By using the specific protocol described hereinafter, and in accordance with the foregoing, the present applicant derived the subject hybridoma W11C5.

The monoclonal antibody produced by the selected clone is then preferably classified to determine its immunotype. The W11C5 monoclonal antibody proved to be an IgG type immunoglobulin whioh was extremely stable on storage at −70° C.

The hybrid cell is generally grown up in culture to yield quantities of monoclonal antibody suitable for purification and further uses.

After harvesting the culture supernatant, the antibody may be purified by concentration by ultrafiltration followed by affinity chromatography.

The purified monoclonal antibody is then available for immunodiagnosis, immunoassay and production of purified antigen as is known in the art.

Antigen may be purified from the crude mixture of soluble babesial antigens obtained from infected erythrocyte stroma by any means known in the art of affinity purification. For example the antigen may be purified by immunoadsorption onto the monoclonal antibody mounted on a suitable support such as agarose beads, acrylic, cellulosic or nitrocellulosic supports. The antibody may be coupled via ligands. The supported antibody may be packed in an affinity chromatography column and equilibrated with a suitable buffer. Optionally the column may also be treated to inactivate any nonspecific binding sites. The crude mixture of soluble babesial protein antigens may be passed through the column to effect binding of the antigen specified by the monoclonal antibody. The bound antigen may be eluted from the column using a suitable elution buffer. The eluted antigen may be further purified and/or concentrated suoh as by dialysis and/or ultrafiltration.

The purified antigen may be used, in conjunction with a suitable adjuvant, as a vaccine, and suitable vaccination trials conducted.

In the present circumstances, antibody purified antigen was used to raise bovine antisera for serological analysis of the efficacy of the antigens produced fermentation as is described hereinafter. The affinity purified antigen may also be used for immunodiagnosis of unknown sera.

Whilst affinity purified antigen may form an acceptable vaccine, in terms of industrial scale production this means of production is insufficient compared to fermentative processes using recombinant DNA technology. This inefficiency arises from the need to prepare large quantities of infected erythrocytes to source the crude antigen mixture.

Accordingly it is desirable to identify babesial genes coding for polypeptides having at least some of the immunogenicity of the antigen of interest such that the genes may be cloned and expressed in appropriate hosts.

There exists many ways by which the gene of interest may be identified. For example, the purified antigen may be partially amino acid sequenced, and corresponding DNA probes synthesized to screen a genomic or cDNA library to identify clones containing homologous DNA sequences.

The said DNA sequences through further manipulation may be expressed to give polypeptides exhibiting the desired immunological characteristics of the antigen.

Alternatively, the babesial gene may be identified by screening of a cDNA expression library constructed from the reverse transcription of babesial poly A+ mRNA using an antibody probe to identify clones expressing antigenic gene product. The library may then be used to provide inserts for expression vectors whioh are in turn used to transform appropriate hosts. The transformed host may be screened for other expression of the gene of interest.

In the process of the invention any suitable expression vector may be utilized. Examples of suitable vectors include bacteriophages such as the derivatives of bacteriophage λ or plasmids such as derivatives of *E. coli* plasmids (e.g. pUR, pUC or p-GEX series). Where the particular polypeptide of interest is most ably expressed by a eukaryotic host, it may be more appropriate to use the derived plasmids of a yeast suoh as Saocharomyces cerevisae.

In the process of the invention any suitable host for the expression vector may be used. Examples of suitable hosts include yeast cells, mammalian cells, insect cells and bacterial cells. Transformants may be isolated by any appropriate means, for example, growth on selective media.

The transformed hosts may then be screened, either by detection of the desired expressed polypeptide using immunoassay or by probing with DNA or RNA probes.

In the preferred case where monoclonal antibodies have been raised against the antigen of choice, immunologioal screening of expressing recombinants is preferred.

The vector/host combination may be chosen such that the expressed polypeptide is just the translation product of the cDNA transcript of the poly A+ mRNA. Alternatively, and more easily, the translation of the cDNA insert of the expression vector is placed under the control of a strong promoter for expression of a host protein by insertion of the cDNA (in the correct reading frame and orientation) within the gene coding for that host protein. The result is that the host strongly expresses a fusion protein comprising the translation product of the cDNA insert coupled to at least part of the host protein.

The selected transformant may be grown up to yield sufficient quantities of expression product having the desired immunogenic properties for use in immunodiagnosis, immunoassay or vaccines.

It will also be appreciated in relation to this invention that one or more "reverse engineering" steps could be utilized in the inventive process wherein in some oases the antigen W11C5 or related antigens may be obtained from sera from vaccinated animals or infected animals using a *B. bovis* expression library which may be cDNA or genomic in origin. In this case the sera would be used as a probe to screen the expression library to isolate W11C5 antigen or related antigens in a similar manner as described above.

In another aspect of the invention it will also be appreciated that the vaccine containing the antigen of interest could also be utilized as a starting material to eventually isolate the W11C5 antigen or related antigen. In this procedure the antigen from the vaccine could be sequenced to obtain a partial amino acid sequence and oligonucleotide probes constructed from the amino acid sequence could be used to screen a *B. bovis* cDNA or genomic library to isolate a gene coding for a related antigen. By using recombinant technology one could then prepare the antigen in large amounts.

The invention also includes within its scope a test kit for diagnosis of babesiosis which includes the monoclonal antibody McAb11C5 or related monoclonal antibodies as well as selected reagents for detection of babesiosis antigen in body fluids such as blood or lymph. In this test kit any suitable label may be used to detect the antigen-antibody reaction and thus this may be IFA, RIA or more suitably enzyme immunoassay such as ELISA. A method of immunoassay using monoclonal antibody McAb11C5 is also included within the scope of the invention.

It will also be appreciated that a monoclonal antibody similar or related to McAb11C5 (i.e. not necessarily reactive with the same epitope) may be obtained by using antigen W11C5 or a similar antigen or related polypeptide instead of the SPA antigen (Soluble Protein Antigen) obtained from a lysate of *B. bovis* infected erythrocytes as described herein.

The invention will be further described hereinafter with reference to the accompanying figures.

DETAILED EXPERIMENTAL PROTOCOLS

1. Preparation of *Babesia bovis* Soluble Protein Antigen (SPA)

Blood was obtained from a hyperinfected solubilize calf (10–15% parasitaemia) infected with the 'S' (Samford) strain of *B. bovis*. Erythrocytes were pelleted by centrifugation (3000 rpm, 20 minutes, room temperature) in a Sorvall GSA rotor. Pelleted erythrocytes were resuspended in five volumes of PBS (phosphate buffered saline) pH 7.2 by inversion of the centrifuge bottle. PBS-washed erythrocytes were centrifuged as before and the washing procedure repeated.

To prepare 100% infected cells, washed erythrocytes were pelleted as described above and small samples of the erythrocytes treated with 5 volumes of NaCl solutions ranging from 0.15 to 0.85% NaCl to determine the concentration effecting lysis of uninfected cells preferentially to infected cells. In this case, the concentration was determined as 0.35% NaCl.

The remaining erythrocyte pellet was resuspended in 5 volumes of 0.35% NaCl and after 15 minutes at room temperature the whole (infected) erythrocytes were pelleted as before. The supernatant containing red cell "ghosts" and cell debris was discarded.

The infected erythrocyte pellet was resuspended in one volume of PBS pH 7.2 and the suspension passed through a Whatman CF11 cellulose column (pre-equilibrated with PBS p 7.2) to remove white blood cells and platelets. The highly visible infected erythrocyte band was eluted with 2-3 column volumes of PBS.

The infected erythrocytes were centrifuged as before and the resulting pellet resuspended in PBS pH 7.2 to give a 50% suspension of 100% infected erythrocytes.

Lysis of infected erythrocytes was accomplished by the addition of 5 volumes of distilled water. After 5 minutes at room temperature with mixing, the lysate was centrifuged (10,000 rpm, 30 minutes, 4° C.) in a Sorvall GSA rotor and the supernatant containing the erythrocyte cytosol discarded. The pelleted parasites and cell debris were resuspended in one volume of PBS pH 7.2 and the suspension sonicated (100 Watts, 3-5 minutes) to disrupt and solubilize parasites and infected red cell stroma.

The sonicate was centrifuged (105,000×g, 60 minutes, 20° C.) in a Beckman Ti 60 rotor to sediment the cell debris. The supernatant containing the soluble protein babesial antigen (SPA) and soluble red cell material was retained and stored in 10 ml aliquots at −70° C.

2. Identification of SPA Immunoprotective Fraction

To a gel filtration column (BIO-RAD, BIOGEL A5M) equilibrated with isotonic saline was added 1 quarter column volume of the crude soluble protein antigen (SPA) fraction prepared as above. The column was run with 5 volumes of saline yielding two visible bands, the first pigmented band corresponding to hemoglobin complexed with babesial and erythrocytic proteins and the second pigmented band corresponding to normal oxyhemoglobin.

As the first pigmented band eluted from the column it was collected (half column volume) and was concentrated to the original volume by dialysis against polyethylene glycol (CARBOWAX, MW 20,000).

500 microliter aliquots of this fraction were electrophoresed (1% agarose gel, type C, Pharmacia AB) in pH 8, 6, ionic strength 0.1 veronal acetate buffer for approximately 2 hours at 150 volts to separate the soluble proteins. The typical $\beta$ fraction hemoglobin complex band may be visualized in the gel by its pigmentation and this pigmented band was excised from the gel.

Analysis of this gel slice (the $\beta$ fraction) by immunoelectrophoresis and hemagglutination assay showed that the majority of the soluble babesial antigens migrated with the $\beta$ fraction hemoglobin complex. It is surmised that the hemoglobin exhibits non specific binding affinity to many proteins including the majority of the subject basesial antigens as a consequence of lipid peroxidation.

The excised gel slice was comminuted to a particle size suitable for use directly as a vaccine in a tissue grinder with one volume of Freund's Complete Adjuvant (FCA). The crude vaccine so derived corresponds to 2 ml of 100% infected red cells (packed volume).

The crude vaccine so produced wa used to vaccinate cattle and the cattle so vaccinated were homologously challenged with Samford strain Babesia bovis. The crude vaccine was subsequently found to be proteotive against heterologous challenge also.

3. Production of Hybridoma W11C5

Balb/C mice were injected subcutaneously with 100 microliters of the gel slice $\beta$ fraction described above together with 100 microliters of FCA each month for four successive months and then injected on four successive days with the gel slice $\beta$ fraction alone. Splenic cells were harvested from the immunized mice and were fused with myeloma cells from P3-NSI-AG4-1 mice.

Hybrid supernatants were screened by immunofluorescent assay (IFA) and positive wells were cloned and recloned twice by limiting dilution. Clones were than stored in the vapor phase of liquid nitrogen.

The clone designated W11C5 was selected by the following criteria.

By IFA the antibodies secreted by the W11C5 clone stained the infected erythrocyte preferentially with only minor staining of the parasite and with no staining of uninfected erythrocytes (see FIG. 1). This criteria for selection was used on the basis that antibody against the infected erythrocyte should be more effective than antibody raised against the parasite itself, since the parasite and its antigenic epitopes are masked by virtue of the fact that the parasite resides within the infected erythrocyte.

Figure 2:
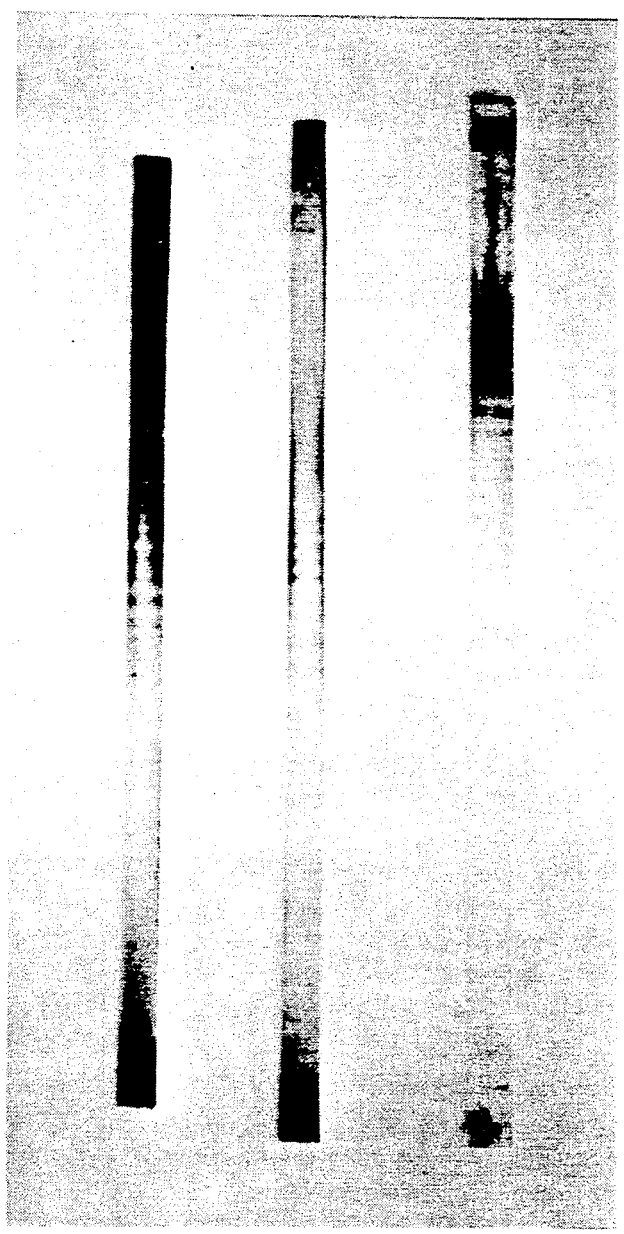
FIG. 2 shows three examples of staining patterns of MAb W11C5 on Western transfers of *Babesia bovis* antigen.

Antigen prepared using the monoclonal antibody excreted by hybridoma W11C5 produced a unique ladder of bands by immunoblotting, starting at approximately 50 kilodaltons (KDa) and increasing in approximately 10 KDa increments. In addition, with some antigen batches, it produced 1 to 4 distinct bands between 200 and 300 KDa (see FIG. 2).

The antigen was also detected by the monoclonal antibody in a heparin fraction of *B. bovis* infected erythrocytes. This fraction has recently been shown to be protective in vaccination studies (Goodger et al., Int. J. Parasitol. 17 (1987) 935).

The monoclonal antibody was classified as an IgG$_2$ and has been shown to be extremely stable on storage at −70° C.

4. Purification of MAb W11C5 and W11C5 Antigen

The W11C5 monoclonal antibody was purified by affinity chromatography utiizing a column containing $\beta$ fraction antigens bound to CNBr-Sepharose 4R (5 mg $\beta$-fraction bound to 1 ml of Sepharose beads). Purified antibody was eluted from the column with 0.2M glycine-HCl pH 2.8 containing 5% NaCl. The pH was restored to neutrality and the eluate stored at −70°C.

W11C5 monoclonal antibody purified as above (25 milligrams) was coupled to CNBr-Sepharose. 20 ml of oxyhemoglobin depleted *B. bovis* antigen (SPA) was reacted with the column which was then washed with PBS until the eluate gave zero absorbance at 280 nanometers.

The column was then washed with 2 column volumes of 0.025M NaBorate, 0.01M Boric acid, 0.1% Tween 20, 1M NaCl to remove non-specifically bound proteins. The bound antigen was then eluted with 0.2M glycine-HCl pH 2.8 containing 5% NaCl. The neutralized eluate was tested for the presence of W11C5 antigen by enzyme linked immunosorbent assay (ELISA). Elution was continued until no antigen was detected in the eluate. The positive eluate fractions were pooled, concentrated back to 20 ml by ultrafiltration and used for analysis and vaccination of Bos taurus animals.

5. Vaccination Trial Using Antigen Purified by the W11C5 Monoclonal Antibody Four splenectomized calves (free of Babesia spp) were injected twice at 1 month intervals with 2 ml of the W11C5 antigen obtained above in FCA. Six weeks later the calves and a control group of four splenectomized calves, were challenged with the homologous Samford strain of *Babesia bovis*.

The vaccinated calves, comparative to the control animals, had significantly lower parasitaemias throughout the challenge. The probability 'P' value was at the level of 0.006 significance.

Antisera from the vaccinated animals prior to challenge produced similar IFA and Western blotting patterns to those obtained with the W11C5 MAb. (Infected erythrocytes staining was observed in IFA and a characteristic "ladder" was evident on Western blots of *B. bovis* SPA).

The W11C5 antigen has also been shown to be present by positive IFA and ELISA results with W11C5 MAb against infected erythrocytes and SPA from strains of *B. bovis* other than Samford, including Lismore and Ka.

By the same methods, cross-reactive antigen has also been detected in erythrocytes infected with other species of Babesia, namely *B. ovis* and *B. equi*. It is surmised that homologous antigens may also be present in other parasite species. Accordingly it is surmised that the W11C5 antigen or the corresponding analagous antigens isolated from other parasite species and/or strains may provide protection against infection of animals by other species in addition to *B. bovis*.

Cloning and Expression in *E. coli* of W11C5 Antigen

6. Preparation of *B. bovis* Poly A+ RNA a) purification of total RNA

Ten ml of a 50% suspension of 100% infected erythrooytes (*B. bovis* Samford strain) was prepared as described previously. To this was added 10 ml of guanidinium isothiocyanate stock (GI mix) at 60° C. (GI mix consists of 100 g of guanidinium isothiocyanate (Merck) dissolved in 100 ml of double distilled water plus 10.6 ml 1M Tris-HCl pH 7.6, 4.24 ml 0.5M EDTA pH 8.0, 21.2 ml 20% N-lauryl sarcosine, 2.1 ml β-mercaptoethanol, filtered through 0.22 μm Nalgene nitrocellulose sterilizing filter).

The infected erythrocyte/GI mixture was maintained at 60° C. with gentle mixing until the solution became highly viscous, indicating lysis of cells and subsequent release to solution of the babesial nucleic acids. The mixture was sonicated (100 W, 1 minute) to reduce viscosity. Twenty-five ml of phenol (pre-equilibrated with 1M Tris-HCl pH 7.4) was added to the mixture at 60° C. with thorough mixing. Twenty-five ml of NaAc buffer (0.1M NaAc pH 5.2, 10 mM Tris-HCl pH 7.4, 1 mM EDTA pH 8.0) at 60° C. was then added with thorough mixing. Twenty-five ml of chloroform/isoamyl alcohol (24:1) was added and the mixture shaken vigorously for 10-15 minutes at 60° C. After cooling on ice for 45 minutes, the mixture was centrifuged (15 minutes, 5,500 rpm, 4° C.) in a Sorvall GSA rotor and the aqueous (top) phase carefully recovered.

The aqueous phase was re-extracted with an equal volume of phenol/chloroform/isoamyl alcohol (25:24:1) at 20° C. for 5 minutes. After centrifugation (10 minutes, 10,000 rpm, 20° C.) in a Sorvall SS34 rotor, the aqueous phase was again recovered. Extraction as above was repeated using an equal volume of chloroform/isoamyl alcohol and the aqueous phase recovered.

Two volumes of absolute ethanol at −20° C. was added to precipitate the nucleic acids. After overnight incubation at −20° C., precipitated nucleic acids were pelleted (20 minutes, 10,000 rpm, 4° C., SS34 rotor) and redissolved in 12 ml of sterile distilled water. Cesium chloride (4.8 g, Boehringer Mannheim molecular biology grade) was then dissolved in the solution and cleared of insoluble material by centrifugation (10 minutes, 10,000 rpm, 20° C., SS34 rotor).

To a 12 ml polypropylene centrifuge tube was added 4 ml of 5.7M CsCl and the cleared nucleic acid/CsCl solution layered carefully on top. The tube was centrifuged (16 hours, 30,000 rpm, 17° C.) in a Kontron TST 41 swing-out rotor to pellet the RNA.

The RNA pellet was redissolved in 400 μl of sterile water and centrifuged to remove any insoluble material (5 minutes, 14,000 rpm, 4° C., Eppendorf centrifuge). Purified RNA was stored in aliquots at −80° C.

Approximate yield and purity of the RNA solution was determined by measurement of optical absorbance of the solution at 260 and 280 nanometers wavelength (Varian U. V. spectrophotometer). The absorbance at 260 nm is used to quantitate the RNA using the approximation: 1 absorbance unit is equivalent to 40 μg/ml RNA concentration. For pure RNA the ratio of absorbance at 260 nm divided by the value at 280 nm = 2.0.

The integrity of the purified RNA was checked by agarose gel electrophoresis of a 2 μg sample (BRL H6 minigel, 1% agarose, 70 volts, 1 hour, Tris-acetate electrophoresis buffer containing 0.5 mg/liter ethidium bromide). The ribosomal bands appeared intact, thus establishing the integrity of the purified RNA.

b) Selection of poly A+ RNA

Stock solutions for selection of poly A+ RNA were as follows:

Loading buffer: 20 mM Tris-HCl pH 7.4, 1 mM EDTA pH 8.0, 500 mM NaCl, 0.1% sodium dodecyl sulphate (SDS).

2× loading buffer: as above, double concentration.

Elution buffer: 10 mM Tris-HCl pH 7.4, 1 mM EDTA, 0.05% SDS.

Oligo-dT-cellulose (Boehringer Mannheim, 0.2 g) was equilibrated with elution buffer (10 ml) and used to form a column. The column was washed with 10 volumes (5 ml) 1×loading buffer, then 3 volumes (1.5 ml) each of sterile water, 0.1M NaOH/5 mM EDTA and sterile water, followed by 2.5 ml 1×loading buffer.

The purified RNA (400 μl) as prepared previously, was heated (65° C., 5 minutes), chilled on ice, diluted with 400 μl of 2×loading buffer and brought to room temperature (20° C.). The RNA was applied to the column followed by an equal volume of loading buffer. The void material was reloaded followed by 4 ml of loading buffer. The bound RNA was eluted using 2 ml of elution buffer. This eluate was then made 500 mM with respect to NaCl, heated and cooled as before and re-applied to the column which had been regenerated as per the preceding paragraph. The column was washed with 4 ml of loading buffer and the bound RNA eluted with 2 ml of elution buffer. The eluted RNA (poly A+ RNA) was made 200 mM with respect to NaCl and mixed with 2.5 volumes of absolute ethanol at $-20°$ C. After overnight incubation at $-20°$ C., precipitated poly A+ RNA was pelleted (20 minutes, 10,000 rpm, 4° C., Sorvall HB4 swing-out rotor) and the vacuum-dried pellet redissolved in 50 μl of sterile distilled water. Purified poly A+ RNA was stored in 10 μl aliquots at $-80°$ C. Approximate concentration of the RNA was determined by absorbance as described previously.

Integrity of the RNA was gauged by agarose gel electrophoresis as described previously.

The poly A+ RNA showed good size distribution, with most RNA migrating behind the small ribosomal RNA subunit.

7. Construction of λgt11 cDNA Expression Library a) cDNA Synthesis cDNA synthesis was performed using a kit system (Amersham International plc, cDNA Synthesis System) containing standardized Amersham reagents.

First strand cDNA synthesis: To an Eppendorf tube on ice were added: 10 μl 5×first strand buffer, 2.5 μl Na-pyrophosphate, 2.5 μl RNase inhibitor, 5 μl dNTP (deoxynucleoside-triphosphate) mix, 2.5 μl oligo-dT solution, 1.25 μl/12.5 μCi α$^{32}$P-dCTP, 10 μl/5 μg B. bovis (strain) poly A+ RNA (as prepared above) and 13 μl water. After gentle mixing, 4 μl (100 units) of reverse transcriptase was added and the mixture incubated at 42° C. for 40 minutes, and then placed on ice. 1 μl was removed for analysis purposes.

Second strand synthesis: To the remaining reaction mixture on ice were added: 93.5 μl second strand buffer, 12.5 μl (125 μCi) α$^{32}$P-dCTP, 5 μl RNase H, 5 μl DNA polymerase I and 151 μl water. This mixture was incubated at 12° C. for 60 minutes, 22° C. for 60 minutes, 70° C. for 10 minutes, and then chilled on ice. T4 DNA polymerase (2.5 μl /10 units) was then added and the tube incubated at 37° C. for 10 minutes. 12.5 μl 0.5M EDTA pH 8.0 and 25 μl 10% SDS were then added, mixed, and a 1 μl aliquot removed for analysis purposes. The reaction mixture was then phenol extracted by mixing with 300 μl of phenol:chloroform:isoamyl alcohol (25:24:1) for 5 minutes prior to centrifugation (5 minutes, 14,000 rpm, 20° C., Eppendorf centrifuge) to separate phases. The aqueous phase was recovered and the extraction repeated. To the recovered aqueous phase was added an equal volume of 4M ammonium acetate. After mixing, 2 volumes of absolute ethanol at $-20$ C. was added and the mixture snap frozen (15 minutes on dry ice). The mixture was thawed to room temperature with gentle mixing and oentrifuged (10 minutes, 14,000 rpm, 4° C., Eppendorf centrifuge) to pellet cDNA. The cDNA pellet was redissolved in 50 μl of TE buffer (10 mM Tris-HCl, 1 mM EDTA, pH 7.5). An equal volume of 4M ammonium acetate was mixed with the cDNA solution and two volumes of absolute ethanol at $-20°$ C. added to reprecipitate the cDNA. After freezing, thawing and centrifugation as above, the cDNA pellet was washed with 200 μl of absolute ethanol at $-20°$ C., dried under vacuum and redissolved in 20 μl of TE. The cDNA was stored at $-20°$ C.

Calculation of cDNA synthesis efficiency and yield: The 1 μl aliquots previously put aside from the first and second strand synthesis reactions were diluted to 20 μl with water. For each sample, 2 μl of solution was spotted onto two 1 cm filter discs (Whatman DE-81 cellulose) labelled 'A' and 'B'. The 'B' filters were washed six times with 0.5M Na$_2$H PO$_4$ (5 minutes per wash, 20° C.) and rinsed twice in water and then twice in absolute ethanol. All four filters were then dried and counted in a scintillation counter (LKB rack β).

The results for the first strand synthesis were that filter 'A' produced 20,594 cpm and filter 'B' returned 929 cpm, equivalent to 4.5% incorporation of label. Knowing that the total dCTP utilized was 25 nanomoles, we therefore deduce that the total dCTP incorporated was 1.13 nanomoles and therefore that the total dNTP incorporation is 4.51 nanomoles (assuming equal uptake of all dNTP's). From this we can deduce that the weight of the cDNA synthesized was 1.58 micrograms of single stranded DNA. Since 5 micrograms of poly A+ RNA was the starting material, the percentage of RNA transcribed was 31.6%.

On the second strand analysis and by equivalent calculation, the total percent incorporation was 8.74%, and knowing that the total dCTP was 25 nanomoles we know that 1.09 nanomoles incorporated dCTP was the corresponding figure, and that the amount of total dNTP incorporated in the second strand synthesis is therefore 4.36 nanomoles. This relates to an equivalent amount of 1.53 micrograms of second strand cDNA synthesized. As a measure of the efficiency of double stranding of the first strand oDNA the calculated percent of second strand transcribed off the first strand is the percentage ratio of the relative weights, and this leads to a 97% efficiency for production of double stranded DNA from the single strand. By calculation, the total double stranded oDNA produced is therefore 3.06 micrograms. This cDNA provided the source for the cDNA library.

b) Cloning of cDNA into λgt11

Reagents from the Amersham λgt10 cloning system together with prepared λgt11 phage DNA were used to prepare the cDNA for cloning, ligation into vector and in vitro packaging of recombinant phage DNA.

Methylation of B. bovis. cDNA: 1 μl of S-adenosyl methionine (SAM) was diluted to 100 μl with water. To an Eppendorf tube on ice was added 1 μg (6 μl ) of B. bovis cDNA, 4 μl methylase buffer, 2 μl freshly diluted SAM and 6 μl water. After mixing, 2 μl (20 units) of EcoRI methylase was added and mixture incubated at 37° C. for 60 minutes. The tube was further incubated at 70° C. for 10 minutes to inactivate the enzyme and then placed on ice.

Linker addition: To the methylated cDNA on ice was added 3 μl of Linker buffer, 2 μl of EcoRI. linkers and 3 μl of water. After mixing, 2 μl (5 units) of T4 DNA ligase was added and the mixture incubated overnight at 15° C. The mixture was further incubated at 70° C. for 10 minutes to inactivate the enzyme and then placed on ice.

EcoRI digestion to cleave excess linkers: To the ligation mix on ice was added 10 μl of EooRI buffer and 58 μl of water. After mixing, 2 μl (120 units) of EooRI restriction endonuclease was added and the mixture incubated overnight at 37° C. The reaction was then heated (70° C., 10 minutes) and placed on ice.

Removal of excess linkers: A gel filtration column (as supplied by Amersham in cDNA cloning kit) was equilibrated with STE buffer (100 mM NaCl+TE). One hundred μl of the EcoRI digest prepared previously was loaded onto the oolumn and washed-in with 100 μl of STE buffer. Two hundred μl fractions were collected (nine in total) and counted by scintillation to determine the cDNA-containing fractions. These fractions (3 and 4) were pooled. To the pooled fractions was added a 0.1 volume of 3M sodium acetate pH 4.8, and after mixing, 2.5 volumes of ethanol at −20° C. After overnight incubation at −20° C., the precipitated cDNA was pelleted (10 minutes, 14,000 rpm, 4° C.) in an Eppendorf microfuge and the resulting pellet dried under vacuum. The dried oDNA was redissolved in 10 μl of TE buffer. This cDNA solution was used as insert DNA in subsequent cloning steps.

Preparation of λgt11 vector DNA: One hundred micrograms (300 μl) of λgt11 DNA prepared from standard stock phage was added to 40 μl 10×EcoRI buffer (1×EcoRI buffer=10 mM $MgCl_2$, 100 mM Tris-HCl pH 7.5, 50 mM NaCl), 40 μl $H_2O$ and 20 μl (200 u) EcoRI restriction endonuclease (Boehringer Mannheim). The mixture was incubated at 37° C. for 2 hours and then phenol extracted, chloroform extracted and ethanol precipitated as described previously. The precipitated, restricted, phage DNA was washed with 400 μl of 70% ethanol at −20° C., dried under vacuum and redissolved in 40 μl of water. To this solution was added 4.8 μl of 10×calf intestinal alkaline phosphatase (CIP) buffer (1×CIP buffer =10 mM Tris-HCl pH 7.5, 10 mM $MgCl_2$) plus 4 μl of CIP enzyme (88 units, Boehringer Mannheim). After incubation (37° C., 2 hours), the phosphatase reaction mixture was phenol extracted twice, chloroform extracted once and ethanol precipitated as before. After washing with 70% ethanol as described above, the DNA was dried under vacuum and redissolved in 40 μl of TE. The concentration of this vector solution was 2 mg/ml.

Ligation of cDNA insert and λgt11 vector DNA: λgt11 vector (10 μg/5 μl) plus 0.5 μl 0.1M $MgCl_2$ were mixed and incubated at 42° C. for 60 minutes to anneal the phage cohesive termini.

Four tubes labelled 'A' to 'D' were filled as follows:

| Tube 'A': | 2 μg (1 μl) annealed vector + 3.3 μl (approx, 120 μg) cDNA |
|---|---|
| Tube 'B': | 4 μg (2 μl) annealed vector + 3.3 μl (approx, 120 μg) cDNA |
| Tube 'C': | 8 μg (4 μl) annealed vector + 3.3 μl (approx, 120 μg) cDNA |
| Tube 'D': | 1 μg (0.5 μl) annealed vector only |

Water was added to each tube to give a total volume of 8 μl. To each tube was added 1 μl 10×ligation buffer (1×ligation buffer=50 mM Tris-HCl pH 7.4, 10 mM $MgCl_2$, 10 mM dithiothreitol, 1 mM spermidine, 1 mM ATP (adenosine triphosphate), 100 μg/ml BSA (bovine serum albumin)) and 1 μl (6 un) of T4 DNA ligase (Boehringer Mannheim). Ligation was performed overnight at 20° C.

In vitro packaging of recombinant phage: Amersham in vitro packaging mixes were used. Four packaging mixes were used for each ligation reaction 'A' to 'C'. One packaging mix was used to package one quarter of reaction 'D'. For each ligation mixture, the four packaging reactions (incubated for 2 hours at 20° C.) were diluted to 2 ml with TM buffer (10 mM Tris-HCl pH 7.5, 10 mM $MgCl_2$) and a drop of chloroform added as a preservative. The packaging reaction from 'D' was diluted similarly. A further packaging reaction was performed using 100 mg of uncut λgt11 phage DNA and diluted as above. Packaging efficiencies were determined by plating a further dilution of each phage stock produced by in vitro packaging as described above.

Appropriately diluted phage in TM buffer was added to 200 μl of E. coli Y1088 plating oells (plating cells were grown to an O.D. (at 600 nm wavelength) of 1.0, oentrifuged: 3,000 rpm, 10 minutes, 20° C., MSE benchtop centrifuge, and resuspended in 0.1 volumes of TM buffer) to whioh was added 60 μl IPTG (isopropylthiogalactoside, 24 mg/ml, sterile), 4 ml molten top agar (1% Bactotryptone, 0.5% Bacto-yeast extract, 1% NaCl, 0.75% agar) at 50° C. and 60 μl of X-gal (5-bromo-4-chloro-3-indolyl-galactopyranoside, 20 mg/ml in dimethylformamide) prior to plating on a 37° C. prewarmed 9 cm diameter L-agar plate (Luria agar, as for top agar, 1.5% agar). After setting and brief drying, plates were incubated at 42° C. overnight and the phage plaques counted. In the presence of IPTG (inducer) and X-gal (substrate), wild-type λgt11 plaques which express functional β-galactosidase are blue, whereas recombinant phage which express β-galactosidase fusion proteins or truncated β-galactosidase are colourless.

In this experiment, the titre of total plaque-forming units (pfu) from ligations 'A'-'C' was $10^6$ pfu/ml. The titre of clear plaques only, was $7.7 \times 10^5$ pfu/ml (77%). The total number of recombinant phage obtained was $5 \times 10^6$ pfu. Packaging efficiency of uncut gt11 was $6 \times 10^7$ pfu/μg. Packaging of 'D' (vector only) yielded $3.85 \times 10^5$ pfu/μg (blue plaques).

8. Screening of B. bovis λgt11 cDNA expression library using W11C5 MAb

Hybridoma W11C5 was grown in cell culture to yield a supernatant containing the W11C5 MAb. The supernatant was collected and the antibody purified by affinity chromatography on a babesial antigen-cellulose column. Twenty-five ml of purified 11C5 MAb (300 μg/ml protein) was diluted to 100 ml in TBS (Tris-buffered saline: 50 mM Tris-HCl pH 7.5, 300 mM NaCl) made 0.5% with respect to gelatin.

Two hundred thousand recombinants from the cDNA library as prepared above were plated onto four 14 cm diameter L. agar plates (no X-gal or IPTG) using 500 μl of E. coli Y1090 plating cells (prepared as for Y1088 plating cells above) and 10 ml of molten top agar per plate. The plates were incubated at 42° C. until small plaques were just visible (approx. 3 hours) and then overlaid with 13.5 cm nitrocellulose discs (Millipore, 0.45 μm pore size) impregnated with 1 mM sterile IPTG to induce β-galactosidase/fusion protein expression. Orientation marks (3) were made through the nitrocellulose discs using a needle dipped in scripting ink. After a further 3 hours incubation at 42° C., the filters were removed and the plates stored at 4° C. The filters were incubated overnight at 42° C. in 1% gelatin/TBS to block non-specific antibody binding sites. Filters were then incubated with the diluted W11C5 MAb at room temperature for 2 hours. Filters were washed three times in TBS/0.1% Tween 20 (15 minutes, room temperature) to remove unbound MAb. Filters were then incubated for 1 hour at room temperature with 1:300 diluted biotinylated ovine anti-mouse immunoglobulin antiserum (Amersham) in TBS/0.5% gelatin. Unbound antibody was washed off as described previously. Filters were then incubated with streptavidinhorseradish peroxidase conjugate (strep-HRP, 1:300 dilution in TBS/0.5% gelatin, Amersham) for 30 minutes at room temperature. Unbound conjugate was removed (3 washes in TBS, 5 minutes per wash, room temperature). Filters were then incubated in substrate solution (prepared by dissolving 30 mg of 4-chloro-1-napthol (Sigma) in 10 ml of methanol, then adding 10 ml of 10×TBS, 80 ml water and 100 μl of 30% $H_2O_2$ (BDH AnalaR)). All blocking steps, antibody incubations, washes and substrate incubations were done on a rooking platform.

After 15 minutes, filters were removed from the substrate solution, rinsed in TBS and air-dried. Ten clones immunoreactive with MAb W11C5 were clearly visualized as purple spots on the nitrocellulose filters.

9. Generation of pure phage stock and growth of recombinant phaqe

The ten positive clones obtained previously were picked and re-screened at low plaque density through a further two rounds to yield pure, low titre phage stocks. Eight stocks so obtained were plated onto *E. coli* Y1088 at high density (100,000 pfu per 9 cm plate) to give plate lysates. Each plate was then flooded with 5 ml of TM buffer and incubated overnight on a rocking platform at room temperature. The TM was then centrifuged (5,000 rpm, 5 minutes, 4° C., SS34 rotor) to clear. Fifty μl of chloroform was added as a preservative and the phage titre determined. This yielded a high titre phage stock (approximately $10^9$ pfu/ml), stable when stored at 4° C. for several years. The high titre stock of one W11C5-positive clone (designated 11C5.1) was used to construct a lysogenic cell-line in *E. coli* Y1089. To 10 μl of Y1089 plating cells (8×$10^6$ cells) was added 27 μl of 11C5.1 high titre stock (4×$10^7$ pfu), to give a multiplicity of infection (m.o.i.) of 5. The bacteria/phage mixture was incubated at 32° C. for 15 minutes (preadsorption). Lysis of μgt11 is suppressed at 32° C. This mixture was diluted to 1 ml with L-broth (Luria broth: as for L-agar, minus agar) and 10 μl of this further diluted to 1 ml with L-broth. One hundred μl of the second dilution was plated onto an ampicillin-containing L-agar plate (50 μg/ml ampicillin) and incubated overnight at 32° C.

Approximately 70 colonies were obtained. Ten of these were replicated using sterile tooth-picks onto two fresh L-agar/ampicillin plates. One plate was incubated at 42° C. and the other at 32° C. One colony, whioh grew at 32° C. but not 42° C. (a lysogen) was picked from the 32° C. plate and a small culture prepared (50 ml L-broth containing 50 μg/ml ampicillin was inoculated with the colony and incubated overnight at 32° C. with mixing).

This culture was used to prepare glycerol stocks (equal volumes of culture plus sterile glycerol were mixed and stored at −20° C. and −80° C. in duplicates) and to inoculate larger cultures. Two 250 ml L-broth/amp. cultures were inoculated with 2.5 ml of the overnight culture and grown at 32° C. to an O.D. 600 nm of 0.6. Cultures were induced at 45° C. for 20 minutes (shaking water bath) and IPTG added to 1 mM. Cultures were further incubated for 1 hour at 38° C. (with mixing). Longer incubation periods at 38° C. resulted in cell lysis and thus loss of induced fusion protein to culture medium.

The cells were oentrifuged (7,000 rpm, 5 minutes, 20° C., Sorvall GSA rotor) and the pellets promptly resuspended in a total of 10 ml of 'P' buffer (50 mM Tris-HCl pH 7.5, 2 mM EDTA, 0.1 mM dithiothreitol). The suspension was snap frozen in liquid nitrogen and thawed to effect cell lysis, as indicated by high viscosity. The lysate was sonicated (100 W, 1 minute, or until viscosity was low) and centrifuged (10 minutes, 15,000 rpm, 0° C., Beckman J2-21 rotor). The supernatant was decanted, glycerol added to 15% and stored in aliquots at −20° C. The pellet was resuspended in 2 ml of 'P' buffer, glycerol added and stored as for the lysate.

Total protein concentrations of lysate and pellet were determined by the Bradford assay. 5 μl of each was diluted to 100 μl with water and mixed with 3 ml of Bradford reagent (prepared by dissolving 100 mg of Coomassie G250 dye (Aldrich) in 50 ml of absolute ethanol to which was added 100 ml of 85% phosphoric acid and 850 ml water). After 5 minutes at room temperature the absorbance of the solution at 595 nm was determined. This value was converted to protein concentration using a standard (BSA) calibration curve. The protein concentrations of the lysate and pellet were 5 mg/ml and 9 mg/ml respectively.

Identification of 11C5-β-galactosidase fusion protein by SDS-PAGE and Western blotting: 25 μg each of lysate and pellet as prepared above was added to an equal volume of 2×gel loading buffer (4% SDS, 10% β-mercaptoethanol, 20% glycerol, 0.2% bromophenol blue), heated (100° C., 2 minutes) and loaded onto a Biorad Mini Protean II 5% acrylamide SDS-polyacrylamide gel with a 3% stacking gel. (Laemmli, U. K. (1970) Nature 277, 680–685).

After electrophoresis (1 hour, 100 V) the gel (0.75 mm thick) was stained in Coomassie 'R' (0.1% in 10% acetic acid/30% methanol) for 1 hour at 42° C. and destained in the above mixture minus Coomassie 'R' for 2–3 hours with several changes of destaining solution.

Figure 3:
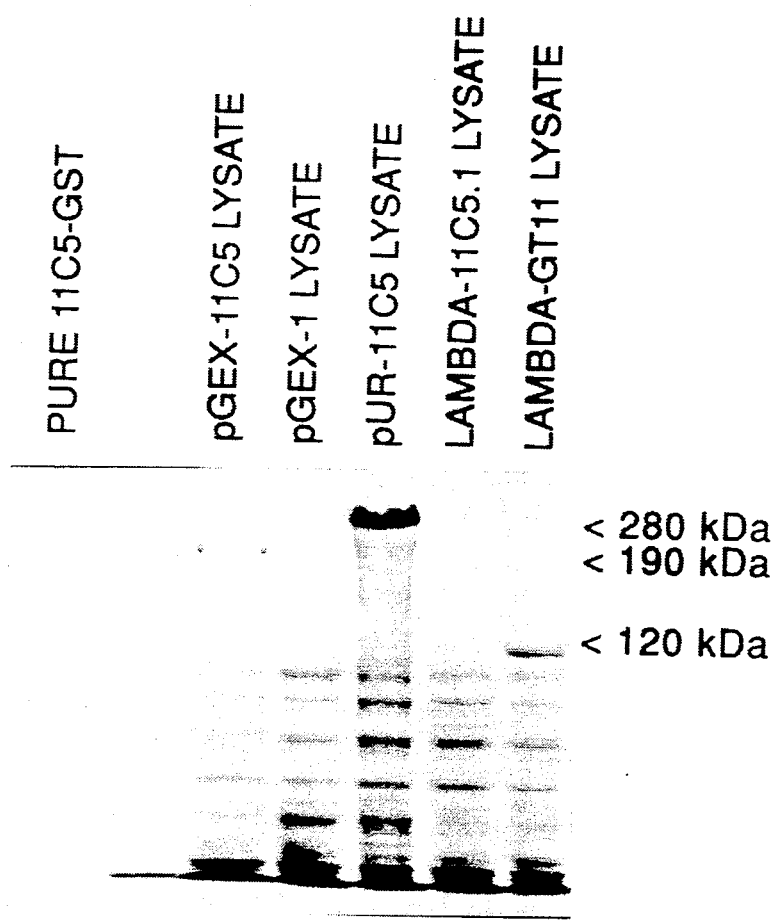
FIG. 3 is a Coomassie stained 5% SDS-polyacrylamide gel showing the relative mobilities of the two different 11C5 fusion proteins.

A protein band of approximately 280 KDa (kilodaltons) was visible in the λ11C5.1 lysogen lysate which was not present in λgt11 wild-type induced lysate (see FIG. 3). The approximately 120 KDa β-galactosidase band present in the λgt11 wild-type lysate was absent from the λ11C5.1 lysate. Thus the clone λ11C5.1 expresses a 280 KDa fusion protein consisting of approximately 160 KDa of 11C5 antigen used with *E. coli* β-galactosidase. Distribution of fusion protein between lysate and pellet fractions indicated fusion protein was present in *E. coli* cells in a predominantly soluble form.

Western transfers of β-galactosidase-11C5 fusion protein in *E. coli* lysate and appropriate controls were made using a Biorad Mini Protean II apparatus with blotting module as per the manufacturers directions. Five percent SDS-polyacrylamide gels were prepared as described previously and blotted for 1 hour at 100 V onto Amersham Hybond C nitrocellulose. Western blots were blocked in 1% gelatin in TBS overnight at 37° C. Antibody screening was performed as described previously for library screening with the exception that HRP-labelled second antibody was used directly rather than a biotinylated second antibody in conjunction with streptavidin-HRP. HRP labelled second antibodies were obtained from KPL inc. and were used at 1:1,000 dilution.

Figure 4:
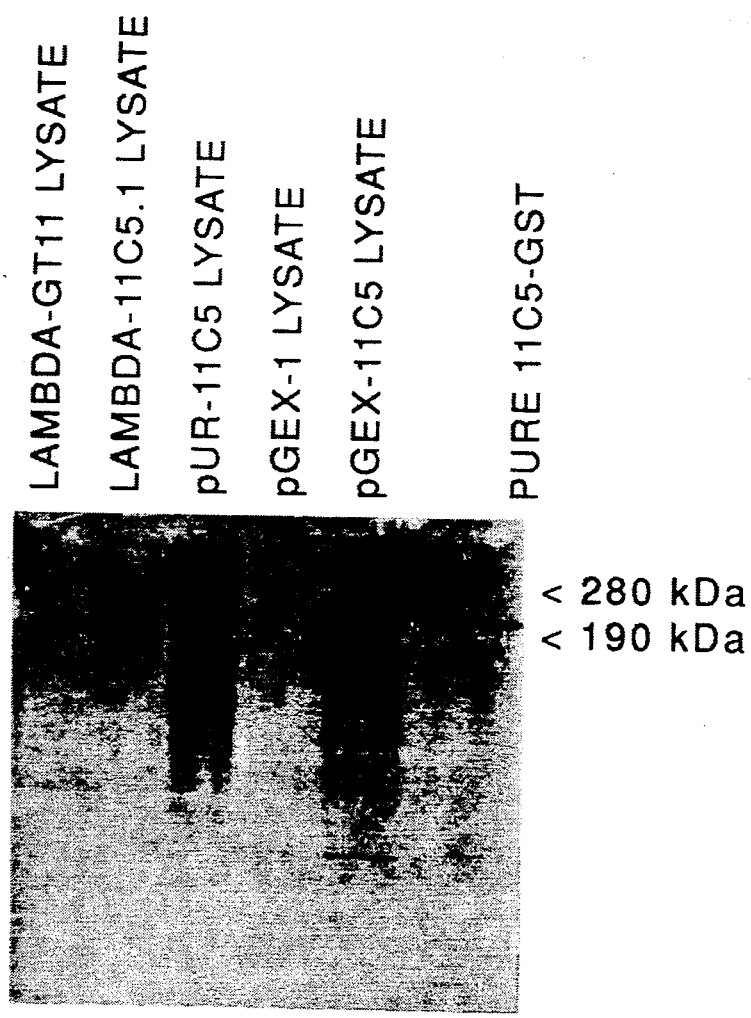
FIG. 4 is a Western transfer of a replica of the gel shown in FIG. 3 probed with W11C5 Mab.

The 11C5-β-galactosidase fusion protein was shown to react specifically with W11C5 MAb, bovine antisera from naturally immune animals (1:600 dilution) and with antisera from cattle immunized with SPA of the lysate of infected cattle (1:600 dilution)(FIG. 4 for example). No significant reaction with these antibody probes was obtained for any natural *E. coli* proteins, including β-galactosidase.

The pattern of bands obtained on the 11C5-β-galactosidase Western (a 'stepladder' of bands of lower molecular weight than the main protein band) is characteristic of this fusion protein and is also observed on Western blots of naturally derived *B. bovis* antigen probed with an anti-11C5 antibody.

10. Vaccination trials using 11C5-β-galactosidase fusion protein

To investigate the efficacy of the 11C5-β-galactosidase fusion protein as a protective antigen, a vaccination trial was undertaken using five groups of six intact adult *Bos taurus* cattle. Cattle were immunized on day 0 and day 28 each with 10 μg of the fusion protein either as an acrylamide slurry cut from an SDS-P.A. gel, or in total cleared lysate (500 μg total *E. coli* protein containing 10 μg fusion protein). Freunds complete adjuvant (FCA, 2 ml) was emulsified with an equal volume of the antigen prior to intramuscular injection. Control vaccination groups received either FCA/PBS only, FCA plus 10 μg β-galactosidase in acrylamide slurry, or FCA plus 500 μg IPTG-induced gt11 wild-type cleared lysate (*E. coli* proteins, including β-galactosidase). Animals were challenged on day 56 with $10^6$ homologous ('S' strain) *B. bovis* parasites injected intravenously. Vaccination groups are summarized below:

Group 1: Naive controls (2 ml FCA+2 ml PBS).
Group 2: β-galactosidase (10 μg ) polyacrylamide gel band.
Group 3: β-galactosidase cleared lysate (500 μg total protein).
Group 4: W11C5-β-galactosidase (10 μg) polyacrylamide gel band.
Group 5: W11C5-β-galactosidase cleared lysate (10 μg in 500 μg total protein).

Figure 5:
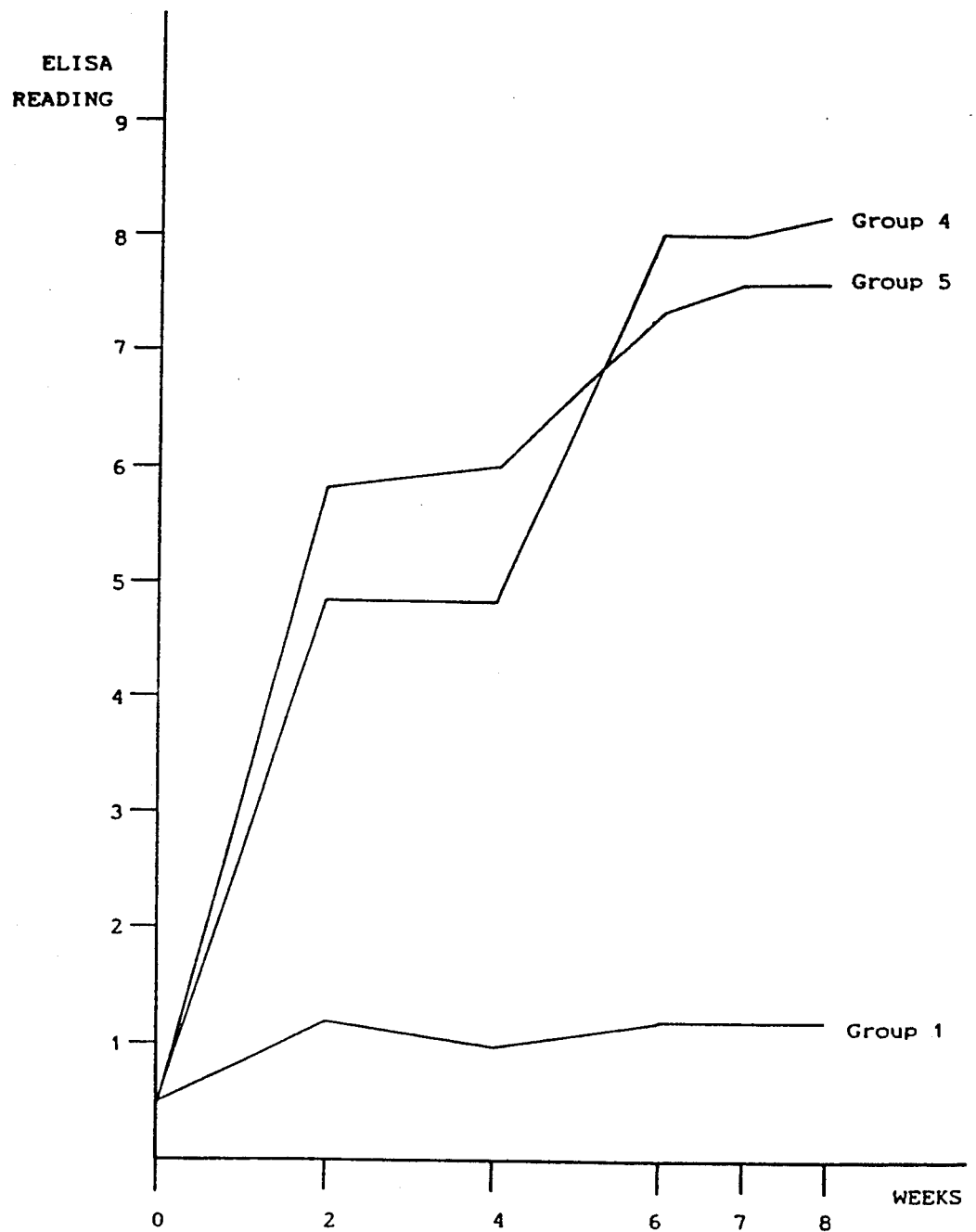
FIG. 5 shows a list of ELISA readings against crude babesial antigen of serum of vaccination groups 1 (naive controls), 4(gel-purified 11C5-B-gal) and 5(crude 11C5-B-gal).

Vaccination groups 4 and 5 (which received gel-purified and crude W11C5-β-galactosidase fusion protein respectively) developed high titres of antibody against the W11C5 antigen as assayed by ELISA using crude W11C5-β-galactosidase antigen. None of the control groups developed significant anti-W11C5 titres. FIG. 5 summarizes ELISA results for the sera of vaccination groups 1-4 and 5. Sera from group 4 and group 5 animals reacted by IFA and *B. bovis*. infected erythrocytes. The pattern of staining obtained by IFA was similar to that obtained using the W11C5 MAb. A serum dilution of 1:1,000 was sufficient to give good IFA staining. Similarly 1:1,000 diluted serum gave a strong signal on Western transfers of parasite and *E. coli* expressed W11C5 antigen and the pattern of immuno-reaction obtained was identical for W11C5 fusion protein antiserum and W11C5 MAb.

Figure 6:
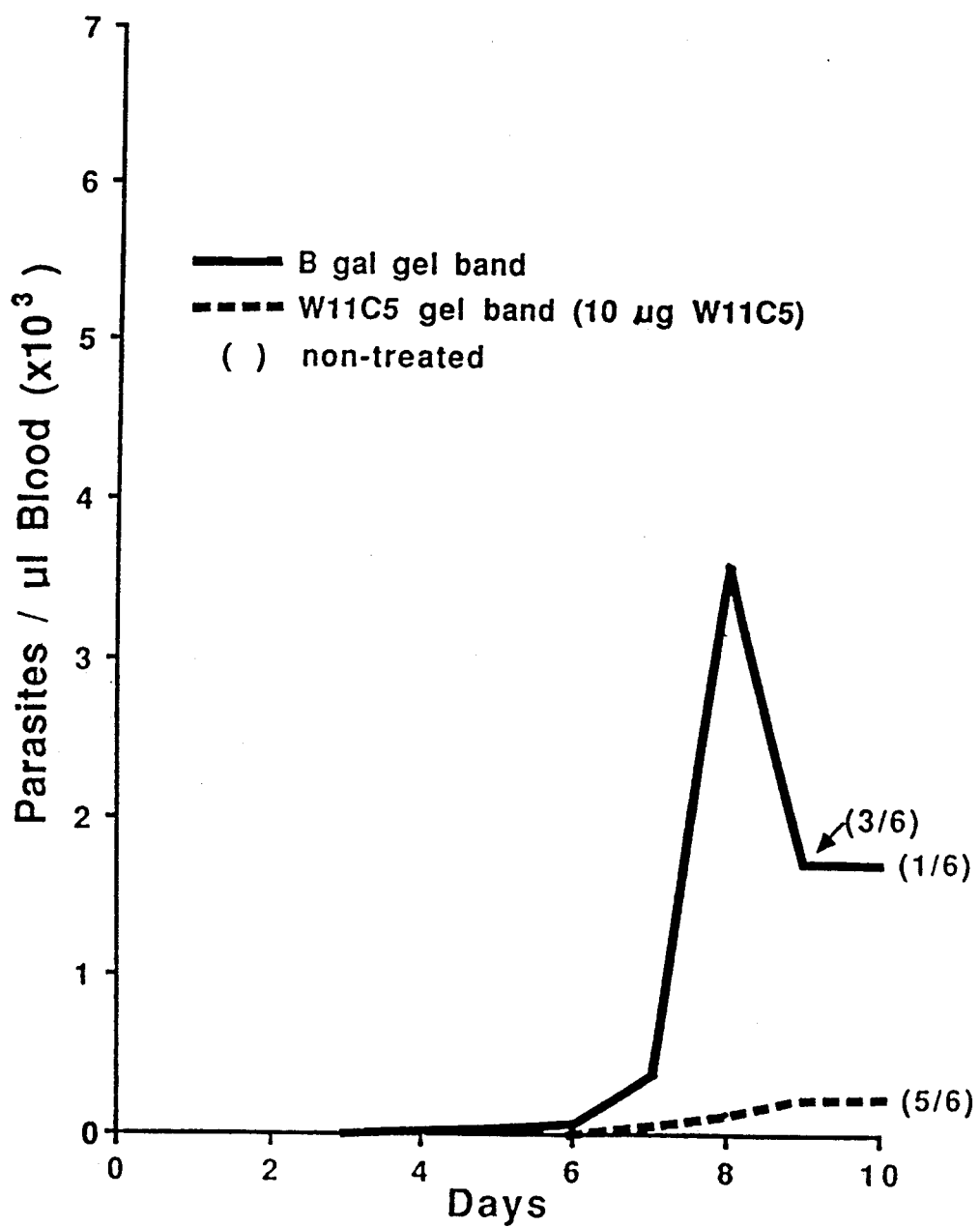
FIG. 6 is a graph showing mean parasitemia and survival of vaccination groups 2 and 4.
Figure 7:
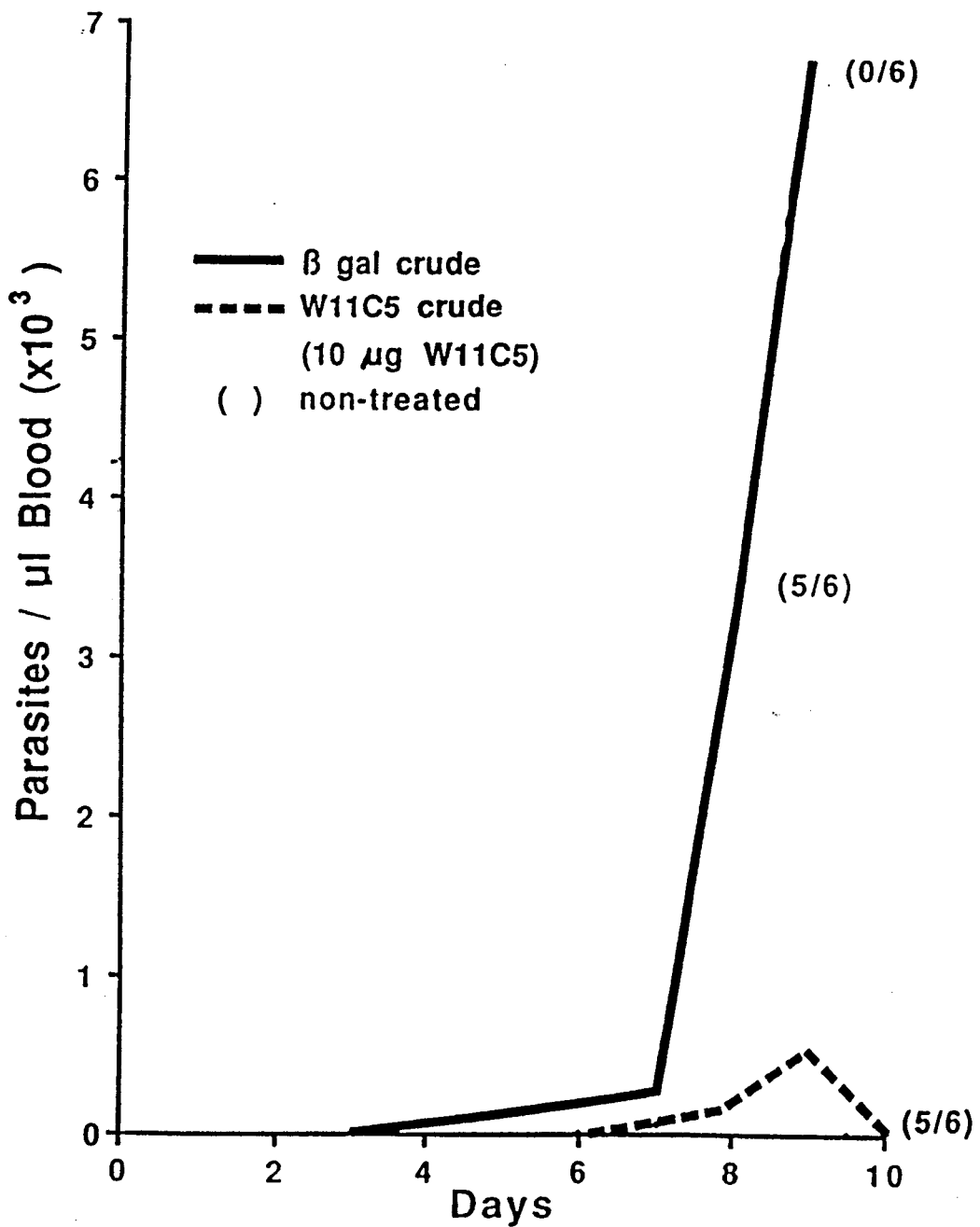
FIG. 7 is a graph showing means parasitemia and survival of vaccination groups 3 and 5.
Figure 8:
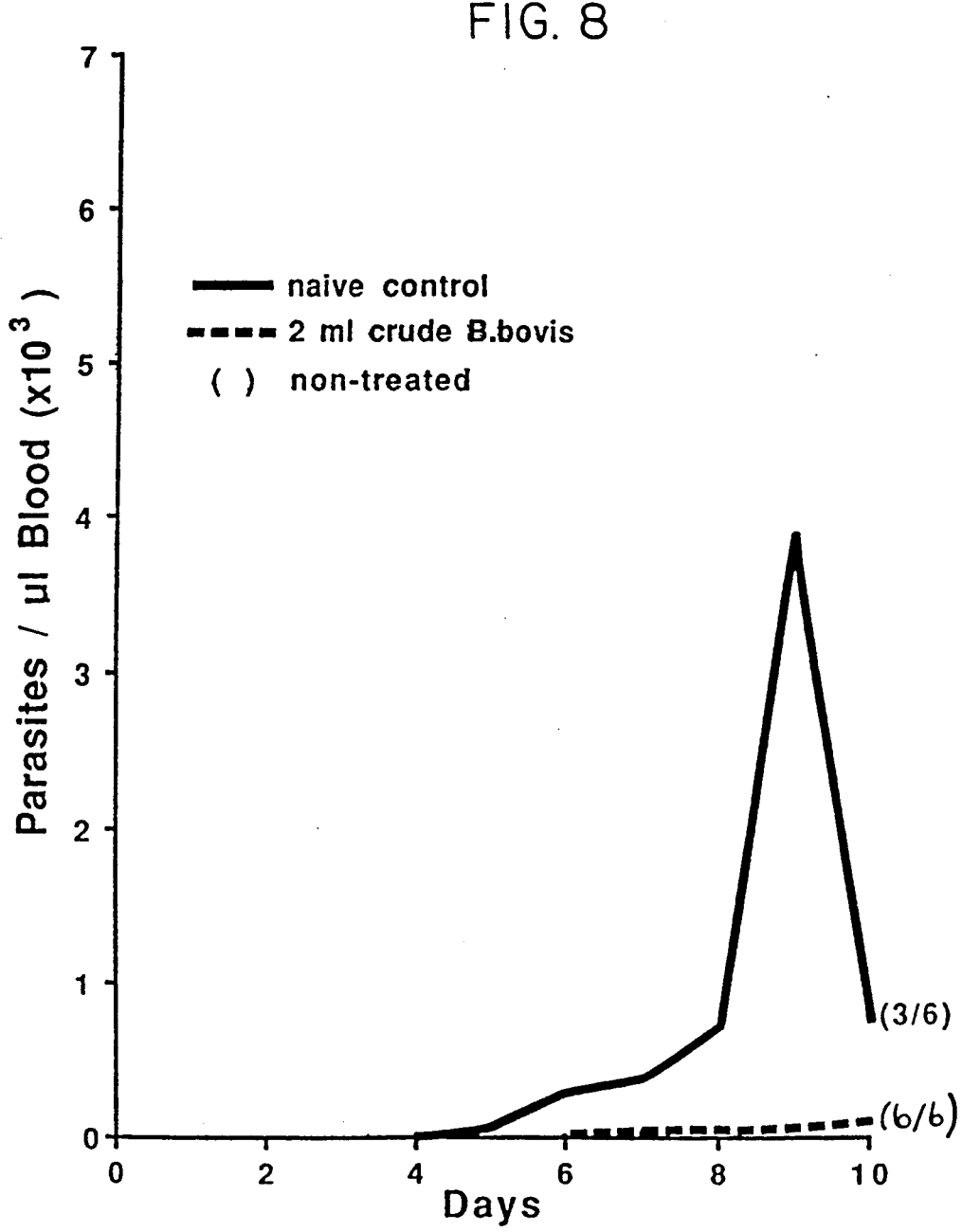
FIG. 8 is a graph showing means parasitemia and survival of vaccination group 1 compared with the results obtained using crude *Babesia bovis* antigen.

On parasite challenge, animals in groups 2 to 5 exhibited immediate elevated temperatures. This is indicative of a hypersensitivity reaction. No such reaction was observed in group 1 naive control animals. Animals in group 4 developed parasitaemias significantly lower than in both the naive controls (P=0.014) and the gel-purifiedβ-galactosidase control group (P=0.034). Animals in group 5 developed significantly lower parasitaemias than those in the corresponding control group which received *E. coli* lysate/β-galactosidase (P=0.028), although the 'P' value obtained by comparison with group 1 naive animals (P=0.059) is not statistically significant (0.05 cut-off). Parasitaemia and survival results are summarized in FIGS. 6-8.

One animal of six in each of the W11C5 vaccinated groups failed to recover naturally after infection (terminally ill animals were drug-treated before death occurred).

Four animals in the naive control group, five in the β-galactosidase gel-band control group and all six animals in the β-galactosidase crude lysate control group failed to survive untreated.

Sera from animals in control groups 1-3 appeared highly jaundiced from day 6-7 onwards (indicating impaired liver function and/or hemolysis) whereas sera from groups 4 and 5 vaccinated animals remained clear.

The high degree of protection conferred by the *E. coli* expressed *B. bovis* antigen used in this vaccination trial is comparable with the protection conferred using crude *B. bovis* antigen.

It was concluded that a pure antigen may be required to abolish the hypersensitivity reaction observed in this vaccination trial. Also it was decided that a heterologous challenge experiment was required to determine whether cross-strain protection was elicited by W11C5 recombinant antigen derived from the Samford strain of *B. bovis*.

11. Patterns of hybridization of the cDNA insert from λ11C5.1 on Southern and Northern blots of *B bovis* genomic DNA and poly A+ RNA The size or sizes of nucleic acid fragments detected on Southern or Northern blots using a specific DNA sequence as a probe is a distinct characteristic of that particular DNA sequence.

Southern Blotting:

The following genomic DNAs were digested to completion using EcoRI: *Bos taurus*, *B. bigemina* (Lismore), *Anaplasma marginale*, *Theileria orientalis* and *B. bovis* (Samford). Each reaction consisted of DNA (4 μg) +3 μl 10×EcoRI buffer +1.5 μl (7.5 units) EcoRI+H₂O to 30 μl. Digestions were performed for 3 hours at 37° C. Digested DNAs were then size fractionated on a 0.8% Agarose gel (BRL H4 apparatus, 40 V, 16 hours) using λ/Hind III and SPPI/RI molecular weight markers (BRESA). Positions of marker bands were marked by injecting the DNA fragments with scripting ink whilst the gel was transilluminated over U.V. The gel was denatured for 40 minutes in 0.5M NaOH/1.5M NaCl and neutralized in 0.5M Tris-HCl/3M NaCl pH 7.0 for 1 hour. The single-stranded DNA was transferred to nitrocellulose (Amersham Hybond C) using 20×SSC as the transfer solution (1×SSC=0.15M NaCl, 0.015M NaCitrate). After marking the position of the wells and DNA standards using penoil, the nitrocellulose filter was baked (2 hours, 80° C.). The baked filter was pre-hybridized overnight, 42° C., (to block non-specific DNA binding sites) in a solution containing: 50% deionized formamide, 3×SSC, 50 μg/ml denatured sheared herring sperm DNA, 10 μg/ml yeast tRNA, 50 mM HEPES buffer, pH 7.0, 5×Denhardts solution (1×Denhardts solution=0.02% Ficoll, 0.02% polyvinylpyrrolidone, 0.02% bovine serum albumin).

Figure 9:
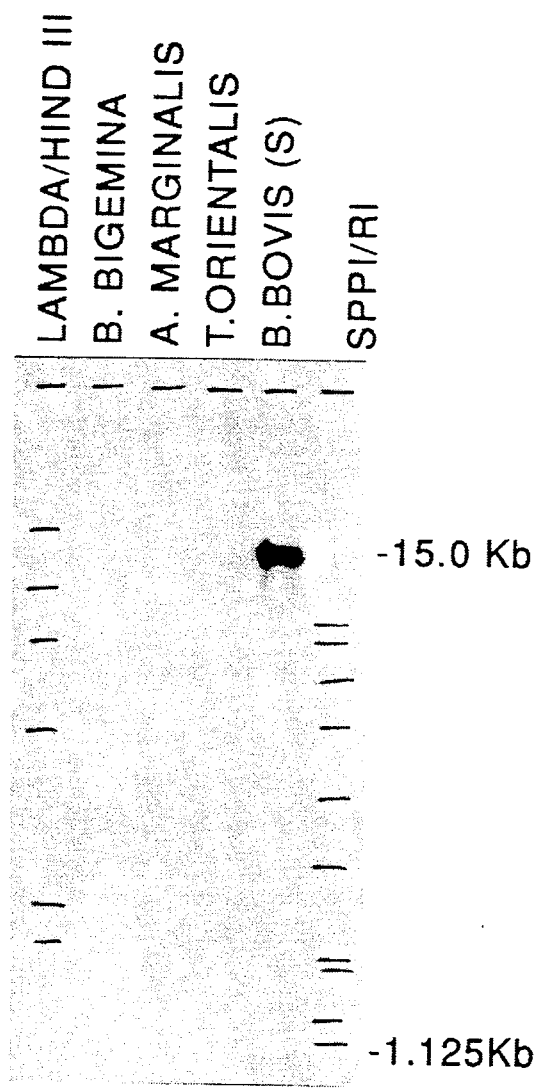
FIG. 9 is a Southern transfer of EcoRI restricted genomic DNA from *B. bigemina* (Lismore), *Anaplasma marginale*, *Theileria orientalis* and *B. bovis* (Samford) probed with the 11C5 cDNA insert.

The λ11C5.1 cDNA insert was radiolabelled using the Amersham 'Multiprime' Kit. DNA was radiolabelled in a reaction mixture containing denatured λ11C5 insert DNA: 25 ng, Multiprime buffer: 10 μl, oligonucleotide primer: 5 μl, DNA polymerase I Klenow fragment: 2 μl, $\alpha^{32}$P dCTP (50 μCi, 3,000 Ci/m mol, Amersham): 5 μl. Incubation was performed overnight at room temperature. Labelled DNA was separated from unincorporated nucleotides by gel filtration using a Pharmacia 'NICK-column' run in T.E. buffer. The labelled DNA was counted (LKB Rackbeta scintillation counter) and the specific activity of the synthesized DNA probe (40 ng) calculated to be $10^9$ dpm/μg. The probe was denatured by boiling, for 5 minutes prior to addition to 10 ml of pre-hybridization solution (as above) and incubation with the prehybridized filter overnight at 42° C. Unbound probe was washed off the filter (3×15 minute washes in 0.1×SSC at room temperature) and the dried filter autoradiographed overnight at −75° C. using a Kodak intensifying screen and Kodak X-Omat AR film. The resulting autoradiogram (FIG. 9) shows that 11C5 cDNA specifically hybridizes with B. bovis DNA (not B. bigemina, Theileria, Anaplasma, or host DNA) in the form of two EcoRI bands of approximately 15.0 Kb (Kilobase pairs of DNA) and 1.25 Kb in length, as judged from calibration data.

Figure 10:
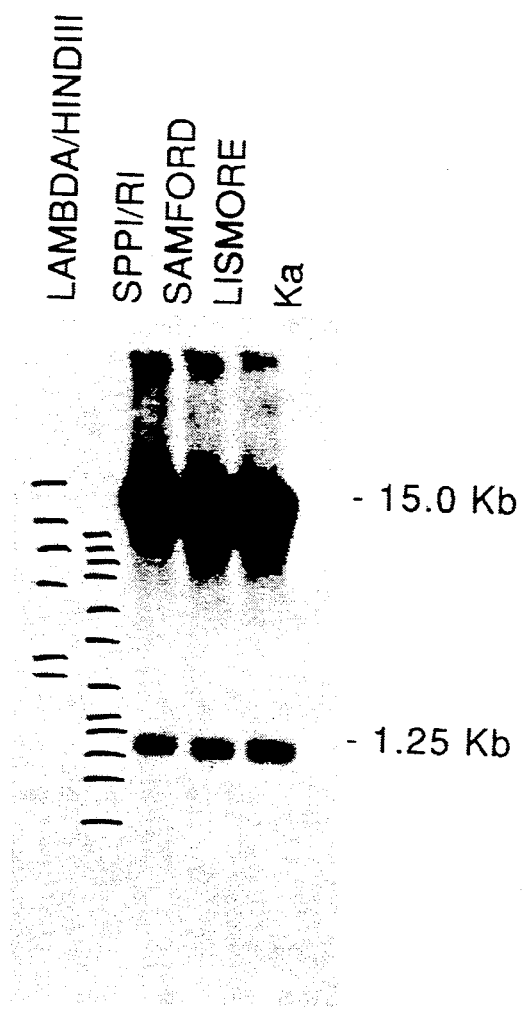
FIG. 10 is a Southern transfer of EcoRI restricted genomic DNA from three different strains of *Babesia bovis* (Samford, Lismore and Ka) probed with the λ11C5 cDNA insert.

A further Southern blot (using a BRL minigel apparatus) of DNA from three B. bovis strains: Samford, Lismore and Ka. (FIG. 10) shows that with EcoRI digestion of the DNA, there is no variation in banding pattern between the three different strains.

Northern Blotting

Running buffer for RNA gels:20 mMNaMOPS, 5 mM NaAc, 1 mM EDTA.

Gel: 1% Agarose, 2.2M formaldehyde, in running buffer.

Sample buffer: 50% formamide, 2.2M formaldehyde in running buffer.

Total cellular RNA (2 μg) from B. bovis (Samford), B. bigemina, Anaplasma marginalis, Theileria orientalis and bovine liver was dissolved in 10 μl of sample buffer, heated at 55° C. for 15 minutes and run on a 1% Agarose-formaldehyde gel with size standards (E. coli rRNA and BRL RNA ladder). The BRL minigel apparatus was run at 70 V for 1 hour.

Figure 11:
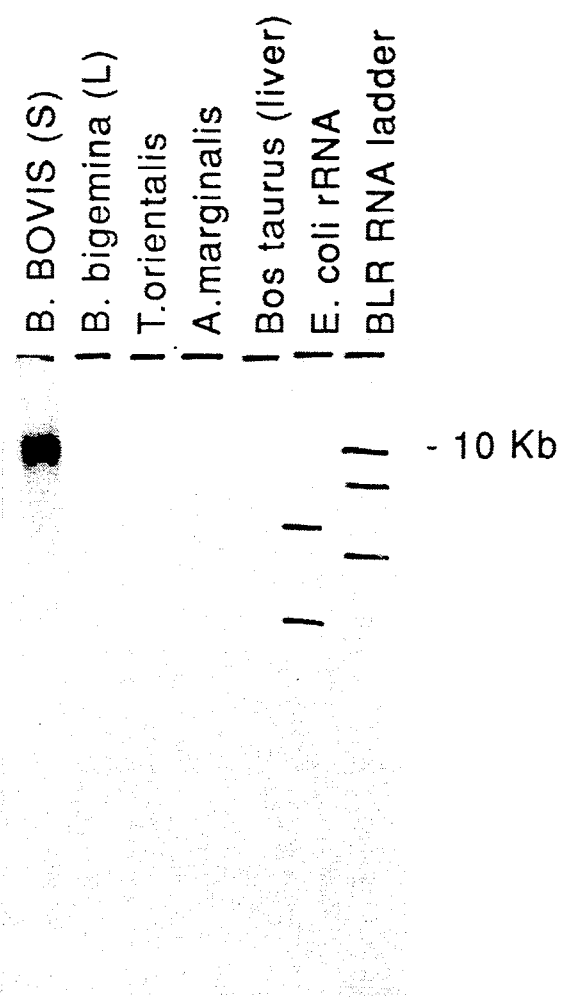
FIG. 11 is a Northern transfer of total RNA from *B. bovis* (Samford), *B. bigemina*, (Lismore), *Theileria orientalis*, *Anaplasma marginale*, and *Bos taurus* (liver) probed with the λ11C5 cDNA insert.
Figure 12:
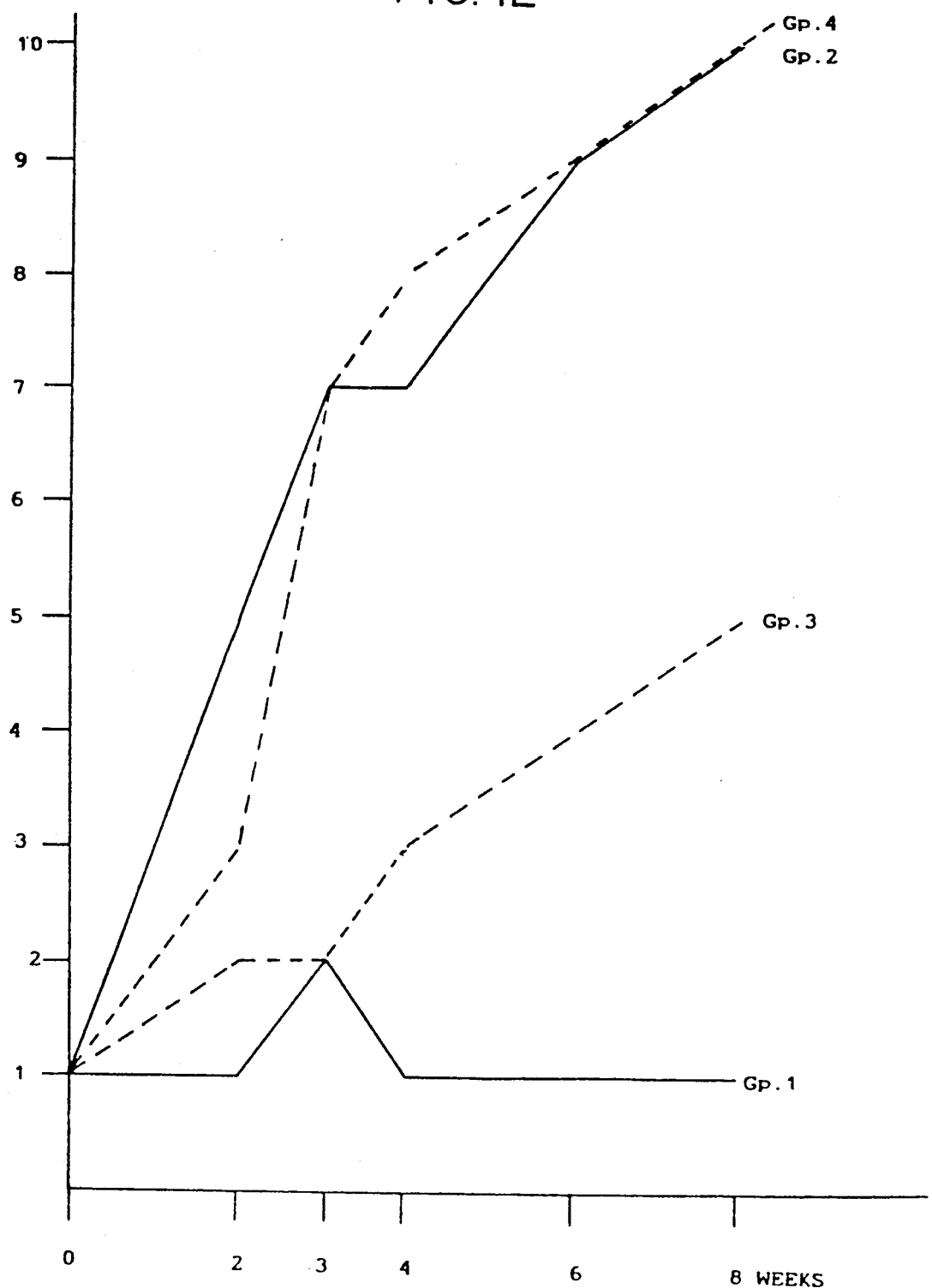
FIG. 12 is a graph of a ELISA against crude babesial antigen for vaccination groups 1 (purified GST), 2 (crude 11C5-B-gal), 3(11C5-GST) and 4(purified 11C5-GST fusion protein).

The gel was soaked in 500 ml of H$_2$O for 30 minutes (to remove formaldehyde) prior to staining in ethidium bromide (500 μg/liter) for 30 minutes. The positions of standards were marked as for Southern blotting. The gel was then denatured for 30 minutes in 50 mM NaOH, 100 mM NaCl and neutralized for 30 minutes in 20×SSC (see Southern blotting). Transfer of RNA to nitrocellulose (Amersham Hybond C) was performed using 20×SSC as the transfer solution. After marking the positions of wells and size standards, the filter was baked (80° C., 2 hours) and pre-hybridized, hybridized with λ11C5 probe, washed and autoradiographed as described for Southern blotting. The resulting autoradiogram (FIG. 11) shows that for the RNA samples used, λ11C5 cDNA hybridizes specifically to B. bovis RNA, in the form of a major 10 Kb RNA band plus a minor 3.4 Kb RNA band.

Sizes of BRESA Molecular Weight Markers Used

1. DNA digested with Hind III: 23130, 9416, 6557, 4373, 2322, 2027, 564 and 125 bp.
2. Phage SPPI digested with EcoRI: 7840, 6960, 5860, 4690, 3370, 2680, 1890, 1800, 1450, 1330, 1090, 880, 660, 480 and 380 bp.

BRL RNA Ladder: 9500, 7500, 4400, 2400, 1400 and 300 bp.

References

A. Southern, E. M. (1979) Standard procedure for transfer of DNA from Agarose gels. Methods in Enzymology 68, 158-159.
B. Maniatis, T. et al. (1982) in Molecular Cloning: A Laboratory Manual pp 202-203. Cold Spring Harbor Laboratory Publications.

12. Partial DNA Sequencing of cDNA Insert from λ11C5.1

The cDNA insert of clone λ11C5.1 was isolated as follows. Whole clone DNA was prepared from λ11C5.1 by the liquid lysate method. E. coli Y1088 plating cells (250 μl ) were mixed with λ11C5.1 phage (from high titre stock described previously) to give a m.o.i. of 0.01. After 15 minutes at 42° C., this mixture was added to 250 ml of L-broth supplemented with glucose to 0.1% and made 10 mM with respect to MgCl$_2$. After overnight incubation at 42° C. with vigorous mixing, 2.5 ml of chloroform was added and the incubation continued for a further 15 minutes to complete cell lysis. Cell lysate was decanted from the chloroform and centrifuged (8,000 rpm, 15 minutes, 4° C., GSA rotor) to pellet cell debris. Phage were precipitated from the supernatant by the addition of 8.75 g of NaCl and 62.5 g of polyethylene glycol 8000 (PEG, Sigma) and incubation overnight at 4° C. Precipitated phage were pelleted (7,500 rpm, 20 minutes, 4° C., GSA rotor) and the drained pellets resuspended in 5 ml of TM buffer. After centrifugation (10,000 rpm, 10 minutes, 4° C., SS34 rotor) to remove debris, the phage suspension was layered onto a stepped CsCl gradient (2 ml steps of 1.7 g/ml, 1.5 g/ml and 1.3 g/ml CsCl in a 12 ml polypropylene centrifuge tube) and centrifuged (32,000 rpm, 2 hours, 18° C., Sorvall TST41 rotor). The pale blue phage band visible between the 1.5 and 1.7 g/ml steps was collected using a needle and syringe. After dialysis to remove CsCl (twice against 2 liters of 25 mM NaCl, 10 mM Tris-HCl pH 7.5, 1 mM MgCl$_2$), RNase and DNase (both supplied by Sigma) were added to final concentrations of 50 μg/ml and 10 μg/ml respectively. After incubation (30 minutes, 20° C.) the suspension was made 10 mM with respect to EDTA, 1% SDS and heated (65° C., 15 minutes). After cooling to 37° C., proteinase K (Sigma) was added to 50 μg/ml and the mixture incubated for 1 hour at 37° C. The mixture was then phenol extracted twice and chloroform extracted once as described previously and then dialyzed three times against 2 liters of TE buffer. Purified DNA was checked by Agarose gel electrophoresis and quantitated by U.V. adsorption (260 nm) using 1 absorbance unit=50 μg/ml DNA. The yield was 1.0 mg.

Purified λ11C5.1 phage DNA (20 μg) was digested to completion with EcoRI (80 μl DNA, 20 μl 10×EcoRI buffer, 5 μl/50 units EcoRI (Boehringer), 95 μl water, 2 hours, 37° C.) and size fractionated through 1% low melting Agarose (BRL Utra Pure) by gel electrophoresis as described previously. The cDNA insert fragment (approximately 3.1 Kb) was excised using a scalpel and extracted from the Agarose by the method of Langridge et al. (Analytical Biochemistry 103, 264-271, 1980). This method relies on the partitioning of the DNA into an organic phase (butanol) in the presence of a nonionic detergent: hexadecyl-trimethylammonium bromide, (C-TAB, Sigma), then re-partitioning into an aqueous phase free from contaminants. 0.6 μg of purified insert (approximately 50% recovery) was obtained.

Ten μg of M13 mp 18 (Pharmacia AB) double stranded DNA (20 μl), 20 μl 10×EcoRI buffer, 160 μl H₂O and 3.5 μl (17.5 units) EcoRI were incubated at 37° C. for 1 hour to digest the DNA. The digested mixture was phenol extracted, ethanol precipitated, spun down and the pellet redissolved in 40 μl TE buffer.

Two μl of insert DNA (approximately 25 ng), 1 μl digested M13 mp18 DNA (0.25 μg), 2 μl T4 DNA ligase (5 units), 1 μl 10×T4 ligase buffer and 4 μl H₂O were incubated overnight at room temperature. The ligation mixture was used directly to transform *E. coli* JM109. Transformation was performed as for plasmid DNA (see following section: Plasmid expression of β-galactosidase-11C5 fusion protein). Approximately 4,000 plaques were obtained. All were blue (non recombinant) except for 20 clear (recombinant) plaques designated mp18-11C5.1 to 20. One plaque was selected (mp18-11C5.4) for further study and preparation of further 11C5-coding insert DNA. A high titre stock of mp18-11C5.4 recombinant phage was prepared by inoculation of a 50 ml culture with a single clear plaque, followed by incubation overnight at 37° C. The cells were spun down and the collected supernatant was the high titre stock containing approximately 10¹² phage per ml.

A 250 ml culture of *E. coli* JM109 was grown to OD₆₀₀=0.6. 1 ml of high titre stock of mp18-11C5.4 clone was added and the culture grown overnight at 37° C. The cells were spun down in 250 ml GSA bottles (7,000 rpm, 10 minutes, 4° C.), and the pellet drained. The pellet was resuspended in 4 ml of 50 mM glucose, 25 mM Tris-HCl pH 7.5, 10 mM EDTA, 5 mg/ml fresh lysozyme and incubated at 20° C. for 10 minutes. Eight ml of 0.2M NaOH/1% SDS was added with gentle mixing and incubated for 10 minutes on ice. Four ml of 3M K Acetate pH 4.8 was added, the mixture vortexed thoroughly and incubated for 30 minutes at 0° C. The mixture was centrifuged (7,000 rpm, 10 minutes, 4° C.) and the supernatant carefully decanted. A 60% volume of isopropanol was added and the mixture incubated for 20 minutes at −20° C. The mixture was centrifuged (10,000 rpm, 10 minutes, 20° C.) and the resulting pellet redissolved in 13 ml of TE buffer. 13.7 g of CsCl (Analar) and 1.3 ml of 10 mg/ml ethidium bromide was added to give a density of 1.56 g/ml. Clarification was performed by centrifugation (10,000 rpm, 10 minutes, 20° C.) and the supernatant centrifuged (45,000 rpm, 40 hours, 20° C.) to band the DNA (Beckman 70 Ti fixed angle rotor). By backlighting the centrifuge tube with long wavelength U.V., it was possible to remove the lower of the two DNA bands visible using a syringe. This contained supercoiled replicative form (R.F.) DNA whereas the upper band contained nicked R.F. DNA and *E. coli* chromosomal DNA. Ethidium bromide was removed by extracting three times with iso-amyl alcohol. The DNA solution was then dialyzed three times against TE buffer to remove CsCl. The insert for further cloning experiments was prepared by EcoRI digestion and subsequent extraction of the insert DNA band from low melting Agarose as described previously. Two other M13 clones (mp18-11C5.3 and 0.8) were grown and analyzed as above. These were found to contain the λ11C5 cDNA insert in each of the two possible orientations. The presence of a SmaI site approximately 0.4 Kb from one terminus of the 11C5 insert was used to identify the two orientations. The SmaI site was subsequently found to be 0.4 kilobases from the 3' end of the expressed cDNA fragment of the 11C5 gene. M13 mp18 clone numbers 3 and 8 were partially sequenced by the dideoxy method as per Sanger et al. (1977). A Biorad sequencing kit was used. This gave the DNA sequence from both ends of the molecule. DNA sequence further into the DNA insert is currently being determined by sequencing particularly deleted clones, constructed as per the Stratagene Cloning Systems Exonuclease/Mung Bean Nuclease Kit. Such deleted clones also enable the DNA sequence to be determined for both strands to give an accurate sequence.

Partial nucleotide sequence and derived amino-acid sequence of the cDNA insert of 11C5.1 is shown in FIG. 19.

13. Plasmid expression of β-galactosidase-11C5 fusion protein

Plasmid pUR288 DNA was digested to completion with EcoRI (5 μg DNA, 5 μl 10×RI buffer, 2.5 μl EcoRI enzyme (12.5 units, Boehringer Mannheim), H₂O to 50 μl final volume; 1.5 hours, 37° C.). The digestion mixture was phenol extracted and ethanol precipitated as described previously. The dried DNA pellet was redissolved in TE buffer. Twenty μl of digested DNA (1.6 μg), 1 μl calf intestinal alkaline phosphatase (CIP, 22 units Boehringer Mannheim), 4 μl 10×CIP buffer and 15 μl H₂O were mixed and incubated for 1.25 hours at 37° C., then 15 minutes at 65° C. to inactivate the enzyme. The phosphatase reaction mixture was then phenol extracted and ethanol precipitated as before.

Ligation of plasmid and insert DNA: Fifty nanograms of digested, phosphatased pUR288 DNA from above (2 μl), 5 μl isolated λ11C5 insert DNA from the M13 sequencing construct mp18 - 11C5.4 (150 ng DNA), 1.5 μl 10×ligase buffer, 1.0 μl T4 DNA ligase (2.5 units, Boehringer Mannheim) and 5.5 μl H₂O were incubated at room temperature for 4 hours before being used to transform *E. coli* JM101.

The transformation protocol used is similar to the method originally developed by Mandel & Higa (1970, Journal of Molecular Biology, 53, p154).

Two 10 ml L-broth cultures of the host cells were grown to an O.D. 600 nm of 0.6 with good aeration at 37° C. The inoculum used was from fresh growth on L-agar. Cells were centrifuged (3,000 rpm, 5 minutes, MSE benchtop centrifuge) and resuspended in 2×5 ml of 0.1M MgCl₂ on ice. Cells were re-centrifuged as before and gently resuspended in a total of 1 ml of 0.1M CaCl₂ on ice. After 30 minutes on ice, competent cells were added to DNA in a small volume of TE or ligation buffer (e.g. 5 μl) with 10 μg of tRNA (transfer-RNA) carrier. The competent cells/DNA mixture was incubated on ice for 40 minutes, heat-shocked (42° C., 2 minutes) and then re-incubated on ice for a further 20 minutes. For M13 RF DNA transformations, transformed cells were mixed with plating cells and plated directly (as for plating phage described previously). For plasmid DNA transformations, transformed cells were diluted to 1 ml with L-broth and incubated at 37° C. for 50 minutes (to allow initiation of expression of antibiotic resistance) prior to plating on antibiotic-containing L-agar (eg 50 μg/ml ampicillin).

Nine transformants obtained by this method using the pUR288/11C5 ligation mixture were used to inoculate 1.2 ml L-broth/ampicillin cultures. After three hours at 37° C., cultures were induced by the addition of IPTG to 1 mM and the incubation continued overnight.

Induced cells were pelleted (5 minutes, 10,000 rpm, 20° C., Eppendorf microfuge) and resuspended in 50 μl of 'P' buffer. Fifty μl of 2×gel loading buffer was then added and the samples boiled for 2 minutes. Twenty μl of each sample was applied to a 5% SDS-polyacrylamide gel and electrophoresed (100 V, 1 hour), stained and destained as described previously. This identified one clone (designated pUR-11C5) which strongly expressed a 280 KDa fusion protein equivalent to that expressed by clone λ11C5.1. The advantages of pUR-directed expression of the β-galactosidase-11C5 fusion protein over λ11C5.1 lysogen-directed expression are: no temperature induction is necessary, all culturing may be performed at one temperature (37° C.), plasmid may be stably maintained in the presence of ampicillin and longer induction times may be used to give high fusion protein yields (no spontaneous lysis of cells). Titration of IPTG used to induce cultures indicates that 0.1 mM IPTG was sufficient to induce expression of fusion protein.

Larger-scale growth of pUR-11C5 directed fusion protein: 250 ml L-broth/ampicillin (50 μg/ml) cultures were grown to OD 600 nm 1.0, IPTG added to 0.1 mM and then cultured overnight at 37° C. Cells were harvested (5,000 rpm, 10 minutes, 4° C., GSA rotor), resuspended in 5 ml of 'P' buffer, sonicated (100 W, 1 minute, to lyse cells and shear DNA) and then centrifuged (15,000 rpm, 20 minutes, 4° C., JA21 rotor). Cleared lysate was made 17% with respect to glycerol and stored at −20° C. Pellet material was resuspended in 2 ml of 'P' buffer and stored similarly. Comparison of lysate and pellet material by SDS-PAGE indicated that the fusion protein remained predominantly soluble when expressed at a high level from the pUR-11C5 construct (see FIG. 3).

14. Subcloning of λ11C5 cDNA Insert into pGEX-1

The plasmid expression vector pGEX-1 was selected for further expression of the λ11C5 cDNA insert due to the possible ease of purification of the resulting antigen-glutathione-S-transferase (GST) fusion protein using glutathione-Agarose beads (Smith, D. B. and Johnson, K. S. (1988) Gene 67, 31–40).

pGEX-1 plasmid DNA was digested with EcoRI, phenol extracted, phosphatased, re-extracted with phenol and ethanol precipitated as before for pUR288. One hundred ng of prepared pGEX-1 vector DNA and 100 ng of λ11C5 cDNA insert DNA (as described previously) were ligated in a 20 μl ligation reaction using 2.5 units of T4 DNA ligase (Boehringer Mannheim) overnight at room temperature. The ligation mixture was used to transform E. coli HB101. Twelve randomly picked transformants were used to inoculate 1 ml L-broth/ampicillin vials and incubated at 37° C. for 3 hours. IPTG was added to 1 mM and the cultures grown overnight. Induced cells were pelleted and resuspended in 50 μl of 'P' buffer. Fifty μl of 2×gel loading buffer was then added, the samples boiled, and 20 μl run on a 10% SDS-PA gel as described previously. Two transformants displayed protein staining profiles with no band at 26 KDa (native GST), but strong bands of approximately 190 KDa (11C5-GST fusion). The 11C5-GST fusion protein was subsequently found to react specifically on Western blots with W11C5 MAb and anti-11C5 bovine polyvalent antisera. One of the two transformants was selected and glycerol stocks prepared as described previously.

The glycerol stock was streaked out on L-agar/ampicillin (50 μg/ml), grown at 37° C. overnight and used to inoculate two 250 ml cultures. At OD 600 nm=1, cultures were induced using IPTG (0.1 mM) and incubated for a further 4.5 hours. Cells were harvested by centrifugation (5,000 rpm, 10 minutes, 4° C., GSA rotor), resuspended in 10 ml of 'P' buffer and lysed by sonication (1 minute, 100 W). The lysate was cleared by centrifugation (10,000 rpm, 15 minutes, 4° C., SS34 rotor) and the resulting lysate and pellet analyzed by SDS-PAGE to confirm high levels of expression (approximately 20%) of a predominantly soluble fusion protein (see FIG. 3).

Purification of 11C5-GST Fusion Protein

The fusion protein as produced by the pGEX-11C5 transformant selected previously was purified from E. coli lysate as follows.

Glutathione-Agarose beads (GA, sulpher linkage, Sigma) were preswollen overnight at 4° C. in TBS and washed three times (centrifuged 2,000 rpm, 10 seconds, 20° C., MSE benchtop centrifuge, resuspended in 50 ml TBS). Two ml of GA beads thus prepared were mixed with cleared lysate (10 ml, as prepared above) for 1 hour at room temperature. The beads were then centrifuged as above and the supernatant removed and stored for further extractions. The beads were then washed three times with 50 ml of TBS/0.1% Tween 20/0.1% Triton X-100/1 mM dithiothreitol (DTT). Bound fusion protein was eluted from the GA beads by mixing the washed beads with 2 volumes of freshly prepared 5 mM reduced glutathione (Sigma)/50 mM Tris-HCl pH 8.0 (final pH 7.5). Purified protein yield was determined using the Bradford assay as described previously. The yield of fusion protein purified from 10 ml of total lysate (50 mg total protein) containing approximately 20% fusion protein was 500 μg (approximately 5% recovery). GA beads were regenerated by washing three times with 3M NaCl followed by three times with TBS. Re-extraction of lysate was repeated several times with little reduction in efficiency. Purity and integrity of fusion protein was determined by SDS-PAGE. (FIG. 3). Also, an endotoxin assay was performed (Limulus assay, CSL laboratories) which indicated less than 2.5 endotoxin units were present in each ml of purified protein.

15. Vaccination trial using W11C5-GST fusion protein

Four groups, each of five adult steers, were used. Animals were injected twice (day 0 and day 28) subcutaneously with antigen in 2 ml of PBS emulsified with 2 ml of FCA. Animals were challenged intravenously on day 56 with $10^7$ B. bovis Lismore strain parasites.

Group 1: 10 μg purified GST
Group 2: 10 μg W11C5-β-galactosidase fusion protein (in crude )ysate)
Group 3: 10 μg W11C5-GST fusion protein (in crude lysate)
Group 4: 10 μg purified W11C5-GST fusion protein.

Animals were bled on weeks 0, 2, 4, 6 and 8 and sera analysis by both IFA and ELISA was performed at a standard 1:500 serum dilution and 1:500 crude lysate B. bovis ('L' strain) antigen dilution. ELISA readings were ranked 0–10 using a hyperimmune serum from a natural infection as the maximum 10 value. Negative sera values ranked 0–1.

Figure 13:
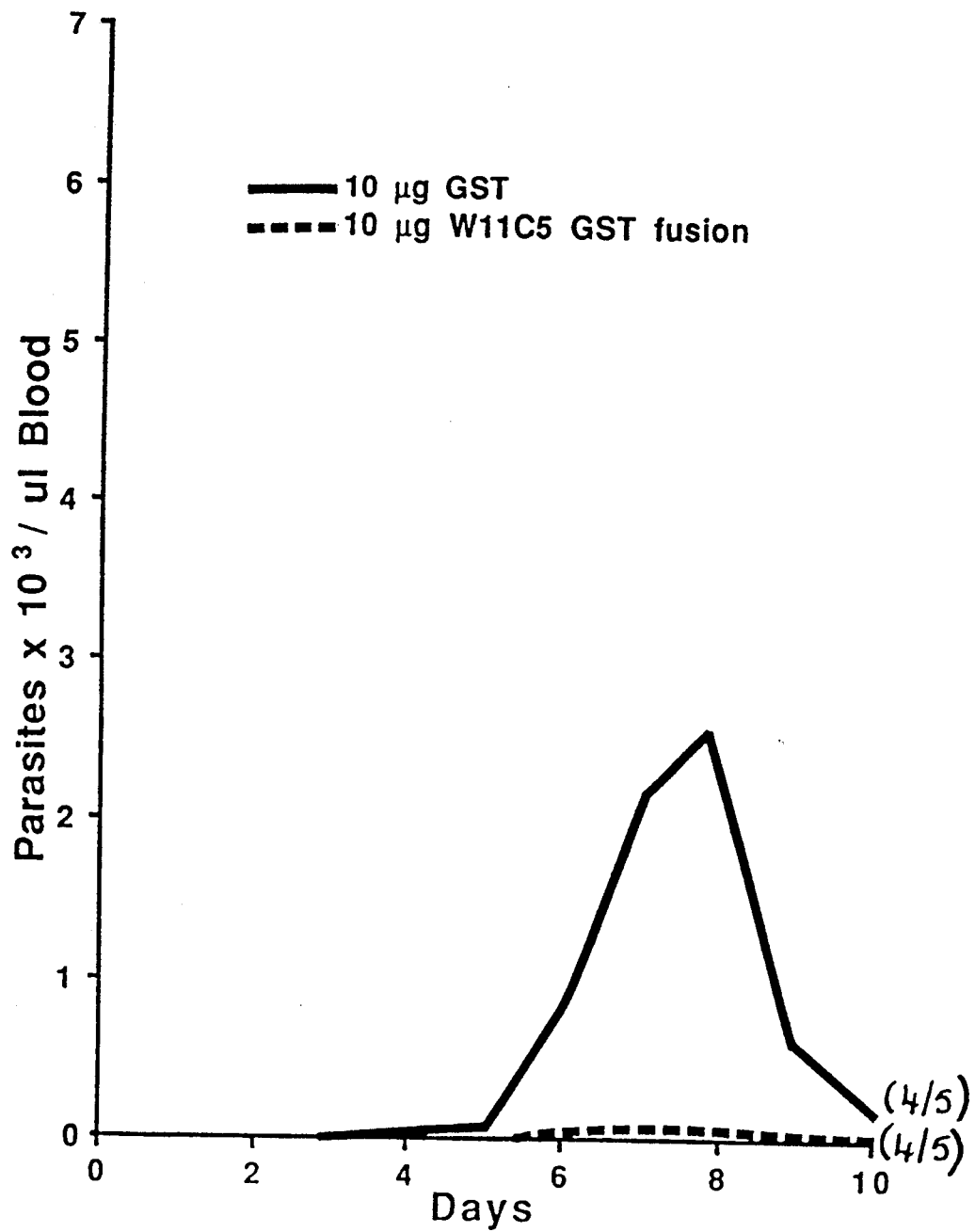
FIG. 13 is a graph showing means parasitemia and survival of vaccination groups 1 (purified GST) and 4(purified 11C5-GST).

All animals in groups 2 and 4 showed uniformly strong serological responses to the W11C5 antigen after four weeks, whilst those in group 3 showed relatively weak responses, even after eight weeks. The data are detailed in FIG. 13.

The IFA pattern of infected erythrocyte staining using sera from W11C5 -GST immunized animals was similar to that obtained using the W11C5 MAb. Sera from those animals also reacted avidly on Western blots of *B. bovis*-derived and recombinant W11C5 antigen and gave the characteristic 'stepladder' pattern.

Figure 14:
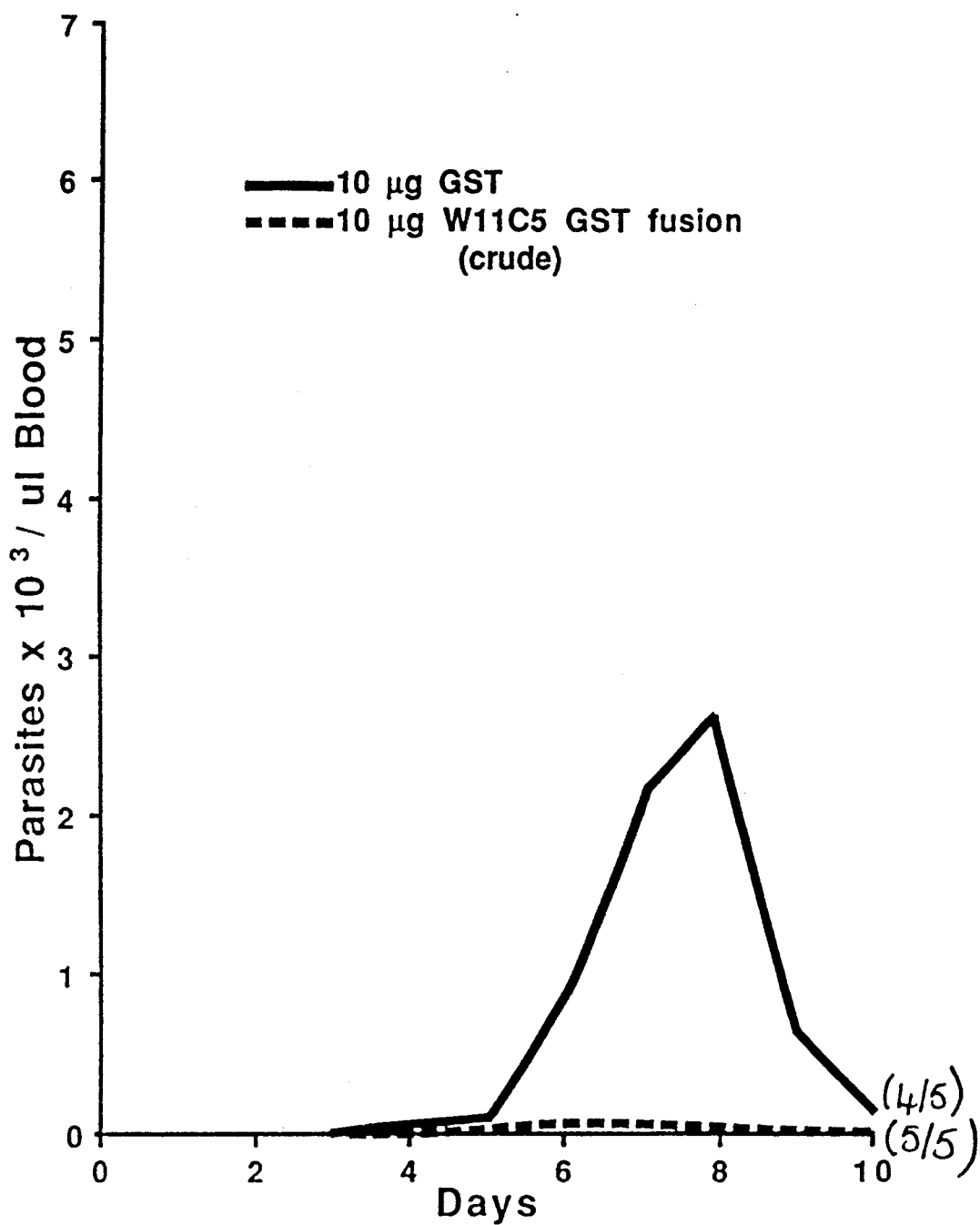
FIG. 14 is a graph showing means parasitemia and survival of vaccination groups 1 (purified GST) and 3(crude 11C5-GST fusion protein).
Figure 15:
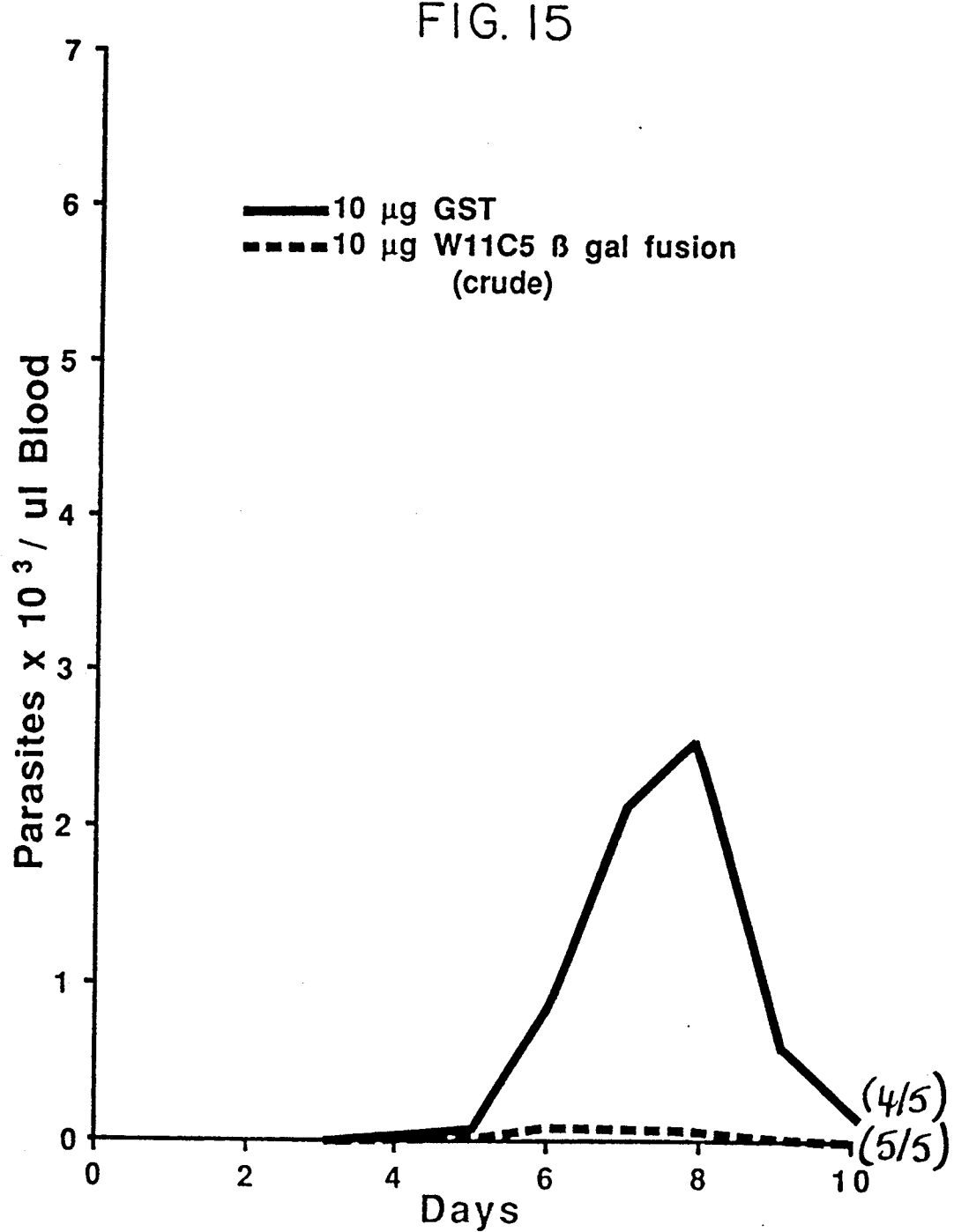
FIG. 15 is a graph showing means parasitemia and survival of vaccination groups 1(purified GST) and 2(crude 11C5-B-gal fusion protein).
Figure 16:
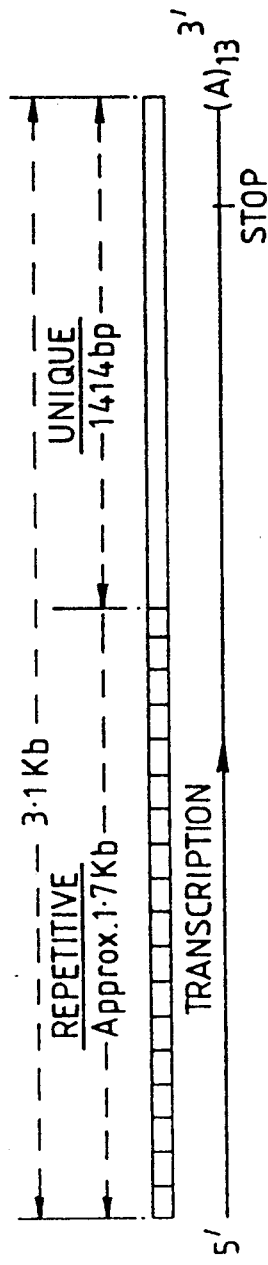
FIG. 16 is a diagram of the W11C5 cDNA structure.

Upon challenge, all vaccinated animals (groups 2-4) showed an immediate increase in temperatures, indicating a hypersensitivity and/or an anaphylactic shock reaction. This was not observed in the GST-vaccinated control group animals. All group 2-4 animals had significant delays in the onset of parasitaemias, as shown in FIG. 14–16. Parasitaemias were significantly different from the controls during this period ($P>0.05-P>0.001$).

Mean maximum parasitaemias were observed on day 8. These were:

| Group 1 controls: | 2680 ± 1438 per $\mu$l blood |
|---|---|
| Group 2 | "104 ± 34 per $\mu$l blood |
| Group 3 | "61.8 ± 28 per $\mu$l blood |
| Group 4 | "76.2 ± 49 per $\mu$l blood |

One of the group 4 animals died on day 12, whilst one of the control animals also required treatment. All controls were severely affected (inappetence, ataxia, high fever). This was not generally the case with the 15 vaccinates. The mean hematocrit fall in the controls was 51%, whilst in the vaccinates it was −35%. A post-mortem examination of the group 4 animal which died showed that the internal organs were heavily congested with unparasitised red blood cells. This animal showed signs of cerebral involvement (impaired balance) prior to death, although its maximum parasitaemia was just 51 parasites per $\mu$l of blood. (Normally, infected erythrocytes are responsible for cerebral babesiosis/organ capillary congestion).

All vaccinated animals had a rapid rebound in their hematocrits by day 11 whereas those of the controls were still depressed.

This vaccination data shows that the W11C5-GST purified fusion data elicits antibody titres which are comparable with those obtained using the W11C5-$\beta$-galactosidase fusion protein. Parasitaemias in these two groups (2 and 4) were also similar; one animal in each group had no detectable parasites.

The crude W11C5-GST fusion protein induced weaker antibody titres and vaccinated animals exhibited a larger hematocrit fall on challenge than the other two vaccination groups although the parasitaemia data were comparable for all three vaccination groups.

All three vaccinated groups (2-4) controlled parasitaemias to levels observed in the previous W11C5-$\beta$-galactosidase and crude *B. bovis* vaccination trials, although differences were not statistically significant throughout this trial due to the lower parasitaemias observed in the control animals.

This vaccination trial demonstrates the ability of W11C5 recombinant antigen derived from the *B. bovis* Samford strain to elicit protection against challenge with the heterologous Lismore strain of *B. bovis*.

It was concluded from this vaccination trial that further work was required to determine the dose of W11C5 antigen, vaccination regime and adjuvant suitable to elicit protective immunity against *B. bovis* without the induction of a hypersensitivity reaction.

We also advise that a sample of the *E. coli* HB101 containing the pGEX-11C5 construct was deposited at the Australian Government Analytical Laboratories, 1 Suakin Street, Pymble, New South Wales 2073, Australia, on Dec. 15, 1988 under accession number 88/39601.

Sequencing of W11C5 cDNA

The cDNA insert of clone λ11C5 was sub-cloned into the plasmid sequencing vector pGEM blue as described previously for sub cloning into pUR322. Sets of nested deletions were generated from both ends of the sub-cloned W11C5 cDNA insert using the exonuclease III/mung bean nuclease system (Bluescript Exo/Mung DNA Sequencing System, Stratagene Cloning Systems, San Diego). Undeleted pGEM-11C5 and deleted derivatives were sequenced using the dideoxy sequencing method (K/RT Sequencing Systems, Promega Biotech, Madison). DNA sequence data was compiled using the Macintosh 'DNA Inspector' computer software.

The W11C5 cDNA structure is shown diagramatically in FIG. 16. The cDNA (approximate length 3100 bp) is composed of a repetitive 5' region (containing approximately 19 copies of a 90 bp repeated DNA sequence in a head-to-tail tandem array) and a unique 3' region 1414 bp in length, which terminates with a row of 13 'A' residues. The unique region DNA sequence and the derived amino acid sequence which terminates with a TGA 'stop' condon at position 1285 in the unique region DNA sequence are shown in FIGS. 17 and 18 respectively.

The DNA sequence of a copy of the 90 bp repeat and the derived amino acid sequenc are shown in FIG. 19. From the amino acid sequence, it is apparent that the 90 bp repeated sequence consists of two sub-repeats of 10 and 20 amino acids in length. From amino acid sequence homology between the two sub-repeats, it is evident that the 20 amino acid repeat may have been generated by an insertion of a DNA sequence block (30 bp in length) into a copy of the 10 amino acid sub-repeat coding sequence. The 10 amino acid subrepeat is encoded by DNA residues 1-30 in the DNA sequence as shown in FIG. 19 and the 20 amino acid repeat by residues 31-90. The proposed inserted sequence is from positions 45 to 75 in the 90 bp repeat DNA sequence. The region from position 54 to 60 bp in the 90 bp repeat is highly variable between different copies of the repeat. Minor variations in other regions of the repeat may occur in a small number of the repeat copies.

The W11C5 cDNA begins at a nucleotide position 2 in a copy of the 90 bp repeat preceded by a 'C' residue from the EcoRI linker used for cloning the cDNA. The repeat region of the cDNA (approximately 1700 bp in length) ends at position 21 in a copy of the 90 bp repeat. The total length of the W11C5 cDNA open reading frame is approximately 3000 bp (encoding approximately 1000 amino acid residues). The estimated size of the W11C5 antigen portion of the W11C5 fusion protein expressed in clone λ11C5 is therefore 120 KDa as judged by DNA sequence data.

Immuno-electron Microscopy Staining of Monoclonal Antibody W11C5 to *Babesia bovis*

The cerebral cortex of cattle acutely infected with *Babesia bovis* was dissected out, fixed and prepared for immunoelectron microscopy. Portions of cerebral cortex were placed in 1% glutaraldeyde, 1% paraformaldehyde, 0.1M- phosphate buffer, 0.08M- sucrose, 0.1 mM-CaCl$_2$, pH 7.4 at 4° C., trimmed to 2 mm$^3$, transferred to fresh fixative at 4° C. for 16h, washed ×3 in fixative buffer, dehydrated in ascending concentrations of ethanol, infiltrated with at least 3 changes of fresh London White Resin (LRW) (1:1 soft: hard) over 24 h placed in fresh resin in gelatin capsules No. 001 which were polymerized 18h 50° C.

Rabbit antiserum to mouse IgG was prepared by the immunization of rabbits with mouse IgG (Gell & Coombs, 1963—in "Clinical aspects of Immunology" 1st. Edition p.7. Blackwell, Oxford) isolated using Protein A Sepharose 4B (Pharmacia). Protein-A gold (9 nm) was prepared (Slot & Geuze, 1985—in European Journal of Cell Biology 38:87-93). Gold sections were out on an LKB ultramicrotome using a glass knife and stained by the sequential application of Monoclonal Antibody W11C5, rabbit antiserum to mouse IgG and Protein-A gold (Slot & Geuze, 1984; "Immunolabelling for electron microscopy" Edited by J. P. Polack & I. M. Vardell, pp. 129-142, Elsevier Science Publishing, Amsterdam). Staining protocol consisted of: 0.02M- glycine, 10 min; wash ×2 PBS, 1% BSA, 5 min; Mab W11C5 diluted 1/20 in PBS, 1% BSA, 60 min, and then washed ×5 PBS, 1% BSA, 5 min; rabbit anti-mouse Ig diluted 1/100 in PBS, 1% BSA, 60 min; wash ×5 PBS, 1% BSA, 5 min; ProteinA-Gold diluted 1/20 PBS, 1% BSA, 30 min; wash ×5 PBS, 1% BSA, 5 min; wash ×4 distiled water, 5 min. Sections were then stained with 2% aqueous uranyl acetate (10 min), lead citrate (1 min) (Reynolds, 1963; Journal of Cell Biology 17:208-000) and viewed in a Phillips S300 transmission electron microscope at an accelerating voltage of 60 keV.

The relative distribution of gold particles was measured from electron micrographs exposed at magnification setting 9 (×16000) to produce prints of whole erythrocytes present within an area of the capillary lumen. Gold particles were counted on the parasite: surface, nucleus, spherical body, rhoptry, other; erythrocyte: membrane, oytoplasm, debris; and capillary lumen for each erythrooyte infected with B. bovis. The number of gold particles in each category was summed and expressed as a percentage of the total count. A minimum of 25 erythrocytes infected with B. bovis were counted and the average and standard error calculated. The gold count was recorded as "Not Present" and not as "zero" when an organelle was absent from the photographic print of the parasite.

Figure 20:
FIG. 20 shows an electron micrograph of immunostained sections of *B. bovis* infected erythrocyte.

Electron micrographs of immunostained sections showed that gold stained mostly a spherical or mitochondrion like organelle at the anterior of the parasite (see lower solid arrow) as well as the membrane of the infected erythrooyte. The gold staining of the erythrocyte membrane appeared to be greater on the stellate projections of the membrane (see solid arrow pointing to right). Other organelles of the parasite and the erythrocyte oytoplasm showed minimal staining (FIG. 20). This shows that the monoclonal antibody W11C5 recognizes a protein within the above organelle as well as a protein located on the surface of the infected erythrooyte.

The invention also includes within its scope the cDNA structure shown in FIG. 16 as well as the sequences shown in FIGS. 17, 18 and 19. The invention also includes within its scope sequences substantially homologous thereto (i.e sequences having greater than 40% homology over a length of 100 nucleotides or longer in the case of a DNA sequence and sequences having greater than 40% homology over a length of 30 amino acids or greater in the case of a protein). The term "substantially homologous thereto" may also include within its scope DNA sequences showing cross-hybridization with the W11C5 cDNA under standard hybridization conditions.

The antigens of the invention are also useful in this invention when used as a vaccine to be protective against babesiosis particularly against homologous challenge (challenge by the same strain or isolate of Babesia) as well as heterologous challenge (challenge by different strains or isolates of Babesia). The antigens may also be protective not only against B bovis but also B. ovis, B bigemina, B canis and other strains of Babesia.

The recombinant antigen when expressed as a fusion protein was expressed at a relatively low level in λgt11. When subcloned into pUR288 higher levels of expression were obtained. When subcloned into pGEX 1 relatively high levels of expression were obtained to facilitate purification.

The claims defining the invention are as follows:

1. A substantially pure 160 kDa babesial antigen which induces protective immunity against homologous or heterologous challenge with babesia, wherein the babesia is selected from the group consisting of B. bovis, B. ovis and B. equis.

2. The substantially pure babesial antigen as claimed in claim 1, wherein the babesia is B. bovis.

3. A substantially pure babesial antigen immunoreactive with monoclonal antibody MAb W11C5 or with antisera raised against native W11C5 antigen or antisera raised against recombinant W11C5 antigen.

4. A substantially pure 160 kDa babesial antigen which induces protective immunity against homologous or heterologous challenge with babesia of cattle, and which is immunoreactive with monoclonal antibody MAb W11C5 drived from hydridoma 88 121501-W11C5.1.A5.F10.A2.

5. A substantially pure babesial antigen which induces protective immunity against homologous or heterologous challenge with babesia, wherein the babesia is selected from the group consisting of B. bovis, B. ovis and B. equis, and wherein said antigen is encoded by a gene consisting essentially of the DNA sequence shown in FIG. 17, and which has a unique region having the amino acid sequence shown in FIG. 18 and a repeat region having the amino acid sequence shown in FIG. 19.

6. The antigen as claimed in claim 5, wherein the babesia is B. bovis.

7. A substantially pure babesial antigen encoded by a gene consisting essentially of W11C5 cDNA as contained in clone pGEX-λ11C5, wherein said cDNA corresponds to Australian Government Analytical Laboratories deposit 88/39601 shown in FIG. 17.

8. A recombinant antigen encoded by the DNA sequence shown in FIG. 17 which is expressed as a fusion protein with β-galactosidase or with gluthathione-S-transferase, and which is protective against heretologous or homologous challenge with Babesia bovis in cattle.

9. A substantially pure polypeptide consisting essentially of the amino acid sequence shown in FIG. 18.

10. A substantially pure polypeptide consisting essentially of the amino acid sequence shown in FIG. 19.

11. A vaccine consisting essentially of an antigen as claimed in claim 1 in combination with an adjuvant.

12. A vaccine consisting essentially of an antigen as claimed in claim 3 in combination with an adjuvant.

13. A vaccine consisting essentially of an antigen as claimed in claim 4 in combination with an adjuvant.

14. A vaccine consisting essentially of an antigen as claimed in claim 5 in combination with an adjuvant.

15. A vaccine consisting essentially of an antigen as claimed in claim 7 in combination with an adjuvant.

16. A vaccine consisting essentially of an antigen as claimed in claim 8 in combination with an adjuvant.

17. A vaccine consisting essentially of an antigen having the immunogenic properties of the amino acid sequence or polypeptide claimed in claim 9 or 10 in combination with an adjuvant.

18. An isolated DNA molecule consisting essentially of the DNA sequence shown in FIG. 17 which when expressed in E. coli produces a protein which is protective against babesiosis when administered as a vaccine to B. bovis and which elicits antibodies showing similar immunological reactivity with MAb W11C5 or antibodies raised against native W11C5 antigen or antibodies raised against recombinant W11C5 antigen.

19. The DNA molecule as claimed in claim 18, wherein said molecule is the cDNA insert contained in clone pGEX-11C5 corresponding to Australian Government Analytical Laboratories deposit 88/39601.

20. W11C5 cDNA consisting essentially of the structure shown in FIG. 16.

21. An isolated DNA molecule consisting essentially of the DNA sequence shown in FIG. 17.

22. An isolated DNA molecule consisting essentially of the DNA sequence shown in FIG. 19.

23. An isolated DNA molecule consisting essentially of a repetitive component of approximate unit length 90 base pairs followed by a unique component of approximately 1414 base pairs consisting essentially of the DNA sequence shown in FIG. 17, which when expressed as a polypeptide induces immunity against babesiosis in cattle.

24. An isolated DNA molecule consisting essentially of a nucleotide sequence which encodes the amino acid sequence shown in FIG. 18.

25. An isolated DNA molecule consisting essentially of a nucleotide sequence which encodes the amino acid sequence shown in FIG. 19.

26. A vaccine consisting essentially of an antigen encoded by the DNA sequence claimed in claim 18 in combination with an adjuvant.

27. A vaccine consisting essentially of an antigen encoded by the DNA sequence claimed in claim 19 in combination with an adjuvant.

28. A vaccine consisting essentially of an antigen encoded by the DNA sequence claimed in claim 20 in combination with an adjuvant.

29. A vaccine consisting essentially of an antigen encoded by the DNA sequence claimed in clam 21 in combination with an adjuvant.

30. A vaccine consisting essentially of an antigen encoded by the DNA sequence claimed in claim 22 in combination with an adjuvant.

31. A vaccine consisting essentially of an antigen encoded by the DNA sequence claimed in claim 23 in combination with an adjuvant.

32. A vaccine consisting essentially of an antigen encoded by the DNA sequence claimed in claim 24 in combination with an adjuvant.

33. A vaccine consisting essentially of an antigen encoded by the DNA sequence claimed in claim 25 in combination with an adjuvant.

34. Monoclonal antibody MAb W11C5 obtained from hybridoma 88 121501-W11C5.1.A5.F10.A2.

35. A monoclonal antibody reactive with a babesial antigen which induces protective immunity against homologous or heterologous challenge with babesia, wherein the babesia is selected from the group consisting of B. bovis, B. ovis, and B. equis, and wherein said antibody recognizes a protein located on the surface of babesia infected erythrocytes and a protein located within a spherical or mitocondrion-like organelle.

36. The monoclonal antibody as claimed in claim 35, wherein the babesia is B. bovis.

37. A test kit which may be used for detection of babesiosis consisting essentially of a monoclonal antibody as claimed in claims 34 or 35, wherein the babesiosis originates from babesia selected from the group consisting of B. bovis, B. ovis and B. equis.

38. The test kit as claimed in claim 37, wherein the babesia is B. bovis.

39. A process for preparation of a babesial antigen which is immunoreactive with MAb W11C5, and when used in a vaccine, is protective against babesiosis comprising the steps of:
(i) preparing nucleic acids from babesia-infected erythrocytes depleted of leukocytes;
(ii) forming a cDNA or genomic library from nucleic acids obtained in step (i);
(iii) screening said library formed in step (ii) with a suitable probe to identify clones of interest;
(iv) excising DNA in said clones which hybridizes to said probe, inserting said DNA into an expression vector, and transforming an appropriate host with the resulting expression vector;
(v) obtaining from said transformed host a recombinant polypeptide, comprising said babesial antigen which is immunoreactive with MAb W11C5, fused with β-galactosidase, wherein said babesial antigen is protective against babesiosis.

40. A process as claimed in claim 39, wherein in step (ii) a cDNA library is formed from reverse transcriptase of babesial poly A+ mRNA.

41. A process as claimed in claim 39 or 40, wherein the probe is selected from monoclonal antibodies or polyclonal antisera raised against babesiosis infected erythrocytes to identify immunoreactive clones.

42. A process as claimed in claim 41, wherein said cDNA library is produced in λgt 11 expression vector and propagated in an E. coli host.

43. A process as claimed in claim 39, wherein the expression vector is pUR288.

* * * * *